US009480807B2

(12) United States Patent
Bowers et al.

(10) Patent No.: US 9,480,807 B2
(45) Date of Patent: Nov. 1, 2016

(54) DEVICE AND METHOD FOR DETECTION AND TREATMENT OF VENTILATOR ASSOCIATED PNEUMONIA IN A MAMMALIAN SUBJECT

(71) Applicant: Elwha LLC, Bellevue, WA (US)

(72) Inventors: Jeffrey A. Bowers, Bellevue, WA (US); Paul Duesterhoft, Issaquah, WA (US); Daniel Hawkins, Pleasanton, CA (US); Roderick A. Hyde, Redmond, WA (US); Edward K. Y. Jung, Bellevue, WA (US); Jordin T. Kare, Seattle, WA (US); Eric C. Leuthardt, St. Louis, MO (US); Gary L. McKnight, Bothell, WA (US); Nathan P. Myhrvold, Medina, WA (US); Michael A. Smith, Phoenix, AZ (US); Clarence T. Tegreene, Mercer Island, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 349 days.

(21) Appl. No.: 14/044,522

(22) Filed: Oct. 2, 2013

(65) Prior Publication Data
US 2015/0090270 A1 Apr. 2, 2015

(51) Int. Cl.
*A61M 16/04* (2006.01)
*A61M 16/00* (2006.01)

(52) U.S. Cl.
CPC ....... *A61M 16/044* (2013.01); *A61M 16/0051* (2013.01); *A61M 16/0443* (2014.02); *A61M 16/0445* (2014.02); *A61M 16/0459* (2014.02); *A61M 2016/0027* (2013.01); *A61M 2205/0205* (2013.01); *A61M 2205/0266* (2013.01); *A61M 2205/3303* (2013.01)

(58) Field of Classification Search
CPC ................ A61M 16/0443; A61M 16/0445; A61M 16/0459; A61M 2205/0266; A61M 16/0434; A61M 16/0436
See application file for complete search history.

(56) References Cited

U.S. PATENT DOCUMENTS

| | | | |
|---|---|---|---|
| 4,091,816 A | 5/1978 | Elam | |
| 4,955,377 A | 9/1990 | Lennox et al. | |
| 5,305,740 A * | 4/1994 | Kolobow | A61M 16/04 128/207.14 |
| 5,638,813 A * | 6/1997 | Augustine | A61M 16/04 128/207.15 |
| 5,765,559 A | 6/1998 | Kim | |
| 7,985,601 B2 | 7/2011 | Healy et al. | |
| 8,042,544 B2 | 10/2011 | Ward et al. | |
| 8,186,351 B2 | 5/2012 | Munro | |

(Continued)

FOREIGN PATENT DOCUMENTS

EP  0 400 778 A2  12/1990

OTHER PUBLICATIONS

"ISO-Polymers"; IGI Cares; one page; created Oct. 2, 2013.

(Continued)

*Primary Examiner* — Peter S Vasat

(57) ABSTRACT

Devices and methods are disclosed herein for preventing or treating ventilator associated pneumonia in a mammalian subject. The device includes an endotracheal tube having an interior surface and an exterior surface; and one or more closed cell layers in contact with the exterior surface and circumferentially surrounding one or more longitudinal portion of the endotracheal tube, wherein the closed cell layer is flexibly shaped to reversibly form a seal in a trachea of a mammalian subject.

17 Claims, 10 Drawing Sheets

(56) References Cited

U.S. PATENT DOCUMENTS

| | | | |
|---|---|---|---|
| 8,394,059 | B2 | 3/2013 | Sahatjian et al. |
| 2003/0041863 | A1 | 3/2003 | Hargis |
| 2003/0114791 | A1 | 6/2003 | Rosenthal et al. |
| 2006/0107962 | A1* | 5/2006 | Ward ............... A61M 16/04 128/207.14 |
| 2006/0116564 | A1 | 6/2006 | Mintchev et al. |
| 2006/0167482 | A1 | 7/2006 | Swain et al. |
| 2006/0264821 | A1 | 11/2006 | Vo et al. |
| 2007/0244550 | A1* | 10/2007 | Eidenschink ........ A61L 29/04 623/1.49 |
| 2008/0210243 | A1 | 9/2008 | Clayton et al. |
| 2008/0257355 | A1 | 10/2008 | Rao et al. |
| 2009/0024054 | A1 | 1/2009 | Lazarus et al. |
| 2009/0107510 | A1 | 4/2009 | Cornish et al. |
| 2009/0165794 | A1 | 7/2009 | Munro |
| 2009/0248141 | A1 | 10/2009 | Shandas et al. |
| 2010/0163023 | A1 | 7/2010 | Singh |
| 2010/0317956 | A1* | 12/2010 | Kartush ............... A61B 5/4041 600/380 |
| 2012/0244097 | A1 | 9/2012 | Lu et al. |

OTHER PUBLICATIONS

Jaeger et al.; "Special Purpose Endotracheal Tubes"; Respiratory Care; Jun. 1999; pp. 661-685;vol. 44, No. 6.

Lendlein et al.; "Biodegradable, Elastic Shape-Memory Polymers for Potential Biomedical Applications"; Science; May 31, 2002; pp. 1673-1676; vol. 296.

Lendlein et al.; "Controlling the Switching Temperature of Biodegradable, Amorphous, Shape-Memory Poly(rac-lactide)urethane Networks by Incorporation of Different Comonomers"; Biomacmolecules; published on Mar. 2, 2009; pp. 975-982; vol. 10; American Chemical Society.

Lorente et al.; "Influence of an Endotracheal Tube with Polyurethane Cuff and Subglottic Secretion Drainage on Pneumonia"; Am J Respir Crit Care Med; published Oct. 18, 2007; pp. 1079-1083; vol. 176.

"Mallinckrodt Intermediate Hi-Lo ET Tubes"; product specification sheet; one page; created Jul. 29, 2013.

"Polyolefin (Polyolefin) Plastic"; UL Data Sheet; one page; created Oct. 2, 2013.

Sengupta et al.; "Endotracheal tube cuff pressure in three hospitals, and the volume required to produce an appropriate cuff pressure"; BMC Anesthesiology; published Nov. 29, 2004; pp. 1-6; vol. 4; No. 8; BioMed Central.

"Veriflex® Shape memory Polymer"; Table of Contents; created Aug. 16, 2013; four pages.

PCT International Search Report; International App. No. PCT/US2014/058839; Dec. 17, 2014; pp. 1-5.

* cited by examiner

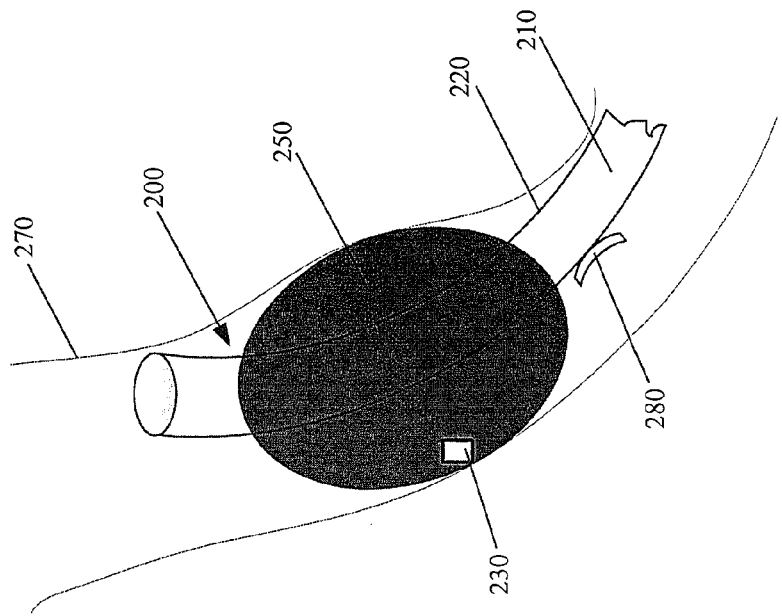
Figure 2B
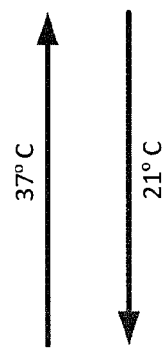
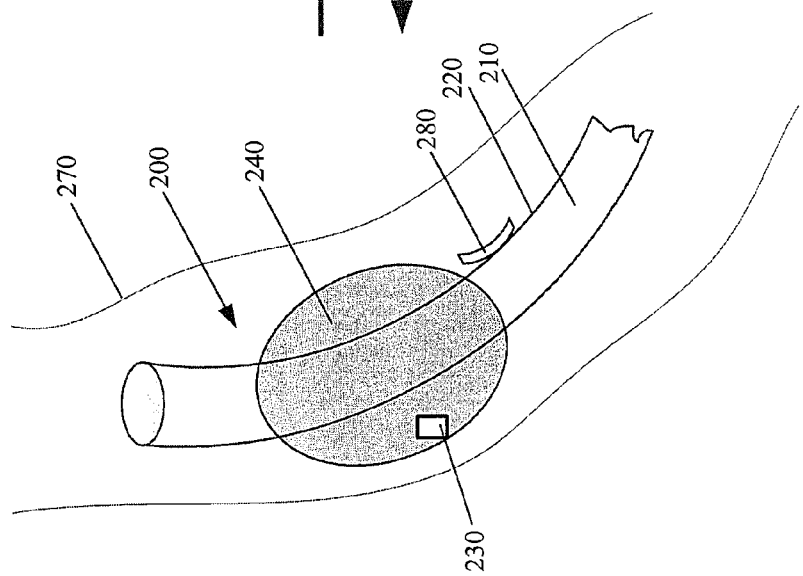

DEVICE AND METHOD FOR DETECTION AND TREATMENT OF VENTILATOR ASSOCIATED PNEUMONIA IN A MAMMALIAN SUBJECT

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None.

RELATED APPLICATIONS

U.S. patent application Ser. No. TO BE ASSIGNED, entitled DEVICE AND METHOD FOR DETECTION AND TREATMENT OF VENTILATOR ASSOCIATED PNEUMONIA IN A MAMMALIAN SUBJECT, naming Jeffrey A. Bowers, Paul Duesterhoft, Daniel Hawkins, Roderick A. Hyde, Edward K. Y. Jung, Jordin T. Kare, Eric C. Leuthardt, Gary L. McKnight, Nathan P. Myhrvold, Michael A. Smith, Clarence T. Tegreene, Lowell L. Wood, Jr. as inventors, filed 2 Oct. 2013 with Ser. No. 14/044,481, is related to the present application.

U.S. patent application Ser. No. TO BE ASSIGNED, entitled DEVICE AND METHOD FOR DETECTION AND TREATMENT OF VENTILATOR ASSOCIATED PNEUMONIA IN A MAMMALIAN SUBJECT, naming Jeffrey A. Bowers, Paul Duesterhoft, Daniel Hawkins, Roderick A. Hyde, Edward K. Y. Jung, Jordin T. Kare, Eric C. Leuthardt, Gary L. McKnight, Nathan P. Myhrvold, Michael A. Smith, Clarence T. Tegreene, Lowell L. Wood, Jr. as inventors, filed 2 Oct. 2013 with Ser. No. 14/044,502, is related to the present application.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

Devices and methods are disclosed herein for prevention or treatment of ventilator-assisted pneumonia (VAP) in a subject utilizing an endotracheal tube. The device includes an endotracheal tube (ET) constructed with a cuff and a sealant to seal the endotracheal tube within the trachea to help prevent infections, including ventilator-assisted pneumonia, in a subject using the endotracheal tube. The sealant may include a thermo-responsive sealant surrounding the cuff of the ET. Alternatively, the sealant may include one or more closed cell layers surrounding the cuff of the ET. Alternatively, the sealant may include an actively-controllable anchoring cuff comprising two or more inflatable balloons in contact with the cuff of the ET.

A device is disclosed that includes an endotracheal tube having an interior surface and an exterior surface; and one or more closed cell layers in contact with the exterior surface and circumferentially surrounding one or more longitudinal portion of the endotracheal tube, wherein the one or more closed cell layers are flexibly shaped to reversibly form a seal in a trachea of a mammalian subject. The device may include two or more of the one or more closed cell layers circumferentially surrounding two or more immediately adjacent exterior longitudinal portions of the endotracheal tube. The one or more closed cell layers may be reversibly compressible closed cell foam layers.

The one or more closed cell layers may include shape memory polymer or syntactic foam. The shape memory polymer may have a glass transition temperature at or above 39° C. and at or below 40° C. The shape memory polymer may have a glass transition temperature at or above 40° C. and at or below 41° C. The shape memory polymer may have a glass transition temperature at or above 41° C. and at or below 42° C. The shape memory polymer may have a glass transition temperature at or above 42° C. and at or below 44° C. The shape memory polymer may have a glass transition temperature at or above 44° C. and at or below 50° C.

The one or more closed cell layers may be configured to seal the endotracheal tube in a trachea of a mammalian subject by contacting the exterior surface of the endotracheal tube and contacting a tracheal tissue of the subject. The device may include a cuff on the exterior surface of the endotracheal tube in contact with the one or more closed cell layers. The device may include a bacteriostatic agent or a bacteriocidal agent in the one or more closed cell layers.

The device may include a temperature sensor configured to measure the temperature of one or more of the one or more closed cell layers and the endotracheal tube. The device may include a controller configured to control a temperature control element in response to a temperature measurement from the temperature sensor. The temperature control element may include one or more of a heating element and a cooling element. The heating element may include in thermal contact with the one or more closed cell foam layers. The cooling element may be in contact with the one or more closed cell foam layers. The heating element may be in thermal contact with the endotracheal tube. The cooling element may be in thermal contact with the endotracheal tube.

A method is disclosed that includes detecting insertion of an endotracheal tube including one or more closed cell layers in contact with an exterior surface of the endotracheal tube into a trachea of a mammalian subject; and adjusting a temperature control element in contact with the endotracheal tube to convert the one or more closed cell layers from non-compressible closed cell layers to compressible closed cell layers. The method may include adjusting the temperature control element in contact with the endotracheal tube to heat or cool the endotracheal tube or the closed cell layers to reversibly convert the closed cell layers from the non-compressible closed cell layers at a temperature below a physiological transition temperature to the compressible closed cell layers at a temperature above the physiological transition temperature. The method may include adjusting the temperature control element in contact with the endotracheal tube to heat or cool the endotracheal tube or the closed cell layers to reversibly convert the closed cell layers from the non-compressible closed cell layers at a temperature above a physiological transition temperature to the compressible closed cell layers at a temperature below the physiological transition temperature. The method may include cooling the endotracheal tube or the closed cell layers to convert the one or more closed cell layers to the non-compressible closed cell layers in order to seal a space between the endotracheal device and the trachea of the mammalian subject. In some aspects of the method, cooling the endotracheal tube or the closed cell layers includes sealing a space between a cuff on the endotracheal device and the trachea of the mammalian subject. The method may include heating the endotracheal tube or the closed cell layers to convert the one or more closed cell layers to the non-compressible closed cell layers in order to seal a space between the endotracheal device and the trachea of the mammalian subject. In some aspects of the method, cooling the endotracheal tube or the closed cell layers includes sealing a space between a cuff on the endotracheal device and the trachea of the mammalian subject. The one or more closed cell layers may include a bacteriostatic agent or a bacteriocidal agent.

The method may include compressing the one or more closed cell layers with a wrap around the one or more closed cell layers. The method may include releasing the one or more closed cell layers from the wrap by chemical attack. The method may include releasing the one or more closed cell layers from the wrap by application of heat. In some aspects of the method, application of heat may be applied resistively.

A device is disclosed that includes an endotracheal tube having an interior surface and an exterior surface; a sealant composition in contact with the exterior surface of the endotracheal tube; and a temperature control element in contact with the endotracheal tube configured to heat or cool the sealant composition to a level required to reversibly convert the sealant composition from a solid sealant composition to a flowable sealant composition. The temperature control element may be configured to reversibly convert the sealant composition from the solid sealant composition at a temperature below a physiological transition temperature to the flowable sealant composition at a temperature above the physiological transition temperature. The temperature control element may be configured to reversibly convert the sealant composition from the solid sealant composition at a temperature above a physiological transition temperature to the flowable sealant composition at a temperature below the physiological transition temperature.

In some aspects, the physiological transition temperature may be at or above 37° C. and is below 39° C. In some aspects, the physiological transition temperature may be at or above 39° C. and is below 40° C. In some aspects, the physiological transition temperature may be at or above 40° C. and is below 41° C. In some aspects, the physiological transition temperature may be at or above 41° C. and is below 42° C. In some aspects, the physiological transition temperature may be at or above 42° C. and is below 44° C. In some aspects, the physiological transition temperature may be at or above 44° C. and is below 50° C.

The sealant composition may be configured to seal the endotracheal tube in a trachea of a mammalian subject by contacting the exterior surface of the endotracheal tube and contacting a tracheal tissue of the subject. In some aspects, sealant composition is in contact with at least the exterior surface of the endotracheal tube. In some aspects, the sealant composition is in contact with a cuff on the exterior surface of the endotracheal tube. A temperature sensor may be configured to measure the temperature of one or more of the sealant composition and the endotracheal tube. In some aspects, the device may include a controller configured to control the temperature control element in response to a temperature measurement from the temperature sensor.

In some aspects, the device may include a reservoir in fluidic communication with the exterior surface of the endotracheal tube and configured to contain the sealant composition. In some aspects, the temperature control element is in thermal contact with the reservoir. In some aspects, the temperature control element is in thermal contact with a fluid conduit connecting the reservoir and the exterior surface. The temperature control element may be in thermal contact with the exterior surface of the tube. The temperature control element may be a cooling element in contact with the endotracheal tube. The temperature control element may be a heating element in contact with the endotracheal tube. In some aspects, the device may include a bacteriostatic agent or a bacteriocidal agent in the sealant composition.

A method is disclosed that includes inserting an endotracheal tube including a sealant composition in contact with an exterior surface of the endotracheal tube into a trachea of a mammalian subject; and adjusting a temperature control element in contact with the endotracheal tube to heat or cool the endotracheal tube and to reversibly convert the sealant composition between a solid sealant composition and a flowable sealant composition. The method may include adjusting the temperature control element in contact with the endotracheal tube to heat or cool the endotracheal tube or the sealant composition to reversibly convert the sealant composition from the solid sealant composition at a temperature below a physiological transition temperature to the flowable sealant composition at a temperature above the physiological transition temperature. The method may include adjusting the temperature control element in contact with the endotracheal tube to heat or cool the endotracheal tube or the sealant composition to reversibly convert the sealant composition from the solid sealant composition at a temperature above a physiological transition temperature to the flowable sealant composition at a temperature below the physiological transition temperature.

In some aspects of the method, the physiological transition temperature may be at or above 37° C. and is below 39° C. In some aspects, the physiological transition temperature may be at or above 39° C. and is below 40° C. In some aspects, the physiological transition temperature may be at or above 40° C. and is below 41° C. In some aspects, the physiological transition temperature may be at or above 41° C. and is below 42° C. In some aspects, the physiological transition temperature may be at or above 42° C. and is below 44° C. In some aspects, the physiological transition temperature may be at or above 44° C. and is below 50° C.

The method may include cooling the endotracheal tube or the sealant composition to convert the sealant composition to the solid sealant composition to a level required to seal a space between the endotracheal device and the trachea of the mammalian subject. In the method, cooling the endotracheal tube may include sealing a space between a cuff on the endotracheal device and the trachea of the mammalian subject. In the method, cooling the endotracheal tube may include cooling the sealant composition. The method may include heating the endotracheal tube or the sealant composition to convert the sealant composition to the solid sealant composition to a level required to seal a space between the endotracheal device and the trachea of the mammalian subject. In the method, heating the endotracheal tube includes sealing a space between a cuff on the endotracheal device and the trachea of the mammalian subject. In the method, heating the endotracheal tube comprises heating the sealant composition.

The method may include measuring a temperature of the endotracheal tube. The method may include measuring a temperature of the sealant composition. The method may include heating the endotracheal tube in response to a measured temperature of at least one of the endotracheal tube and the sealant composition. The sealant composition may include a bacteriostatic agent or a bacteriocidal agent.

A device is disclosed that includes an endotracheal tube having an interior surface and an exterior surface; an actively-controllable anchoring cuff including two or more inflatable balloons configured to contact the exterior surface of the endotracheal tube and configured to contact a trachea of a mammalian subject; a pressure sensor configured to detect pressure of the two or more inflatable balloons; and a controller in communication with the pressure sensor, the controller configured to actively vary pressure within one or more of the two or more inflatable balloons of the anchoring cuff. The anchoring cuff comprising the two or more inflatable balloons may include two or more actively- and independently-controllable inflatable balloons configured for independently varying pressure within the two or more inflatable balloons. The at least one of the two or more inflatable balloons may include an inflatable cuff, circumferentially surrounding a longitudinal portion of the endotracheal tube. The at least two of the two or more inflatable balloons of the anchoring cuff may be positioned at different longitudinal locations along the endotracheal tube. The two or more inflatable balloons of the anchoring cuff may be positioned circumferentially surrounding the endotracheal tube. The controller may be configured to independently vary pressures within the two or more inflatable balloons based on a pre-determined schedule. The controller may be configured to independently vary pressures within the two or more inflatable balloons based on sensor input that detects tissue inflammation. The controller may be configured to independently vary pressures within the two or more inflatable balloons based on a scheduled time at a pre-determined pressure. The controller may be configured to independently vary pressures within the two or more inflatable balloons based on sensor input that detects peristalsis in the esophagus of the subject. In some aspects, the device may include a sensor configured to detect inflammation of tissue proximate the endotracheal tube.

The anchoring cuff including the two or more actively- and independently-controllable inflatable balloons may be configured to maintain rolling contact with the esophagus and a constant position in the esophagus of the subject. The anchoring cuff including the two or more actively- and independently-controllable inflatable balloons may be configured to maintain a rolling toroid. The anchoring cuff including the two or more actively- and independently-controllable inflatable balloons may be configured to maintain three or more azimuthally separated rolling spheres.

In some aspects of the device, a first set of the inflatable balloons may be configured to form a first anchoring cuff, a second set of the inflatable balloons may be configured to form a second anchoring cuff; and the controller may be configured to provide instructions to independently control a pressure of the first set of inflatable balloons relative to a pressure of the second set of inflatable balloons. The controller may be configured to provide instructions to apply a first pressure to each balloon of the first set, and to apply a second pressure to each balloon of the second set. The controller may be configured to set the pressure applied to the first set of balloons to a value below a specified anchor pressure, while setting the pressure applied to the second set of balloons at a value at or above a specified anchor pressure.

A method is disclosed that includes detecting insertion of an endotracheal tube including an actively-controllable anchoring cuff comprising two or more inflatable balloons in contact with an exterior surface of the endotracheal tube into a trachea of a mammalian subject; detecting pressure of one or more of the inflatable balloons with a pressure sensor; and actively varying pressure of the one or more of the inflatable balloons of the anchoring cuff under instructions from a controller in communication with the pressure sensor. The method may include applying pressure under instructions from the controller at or above a specified anchor pressure to a first set of one or more of the inflatable balloons. The anchoring cuff may inhibit motion of the endotracheal tube within the trachea. The method may include applying pressure under instructions from the controller below the specified anchor pressure to a second set of the one or more of the inflatable balloons. The method may include increasing pressure under instructions from the controller of one or more inflatable balloons of the second set to a value at or above the specified anchor pressure, decreasing pressure under instructions from the controller of one or more inflatable balloons of the first set to a value below the specified anchor pressure, wherein the anchoring cuff is configured to inhibit motion of the endotracheal tube within the trachea.

The method may include decreasing pressure under instructions from the controller of one or more of the inflatable balloons to a value below the specified anchor pressure, and wherein the anchoring cuff is configured to extract the endotracheal tube from the trachea. The method may include differentially varying pressures under instructions from the controller of two or more of the two or more inflatable balloons. In some aspects of the method, at least one of the two or more inflatable balloons may include an inflatable cuff circumferentially surrounding a longitudinal portion of the endotracheal tube. The method may include positioning at least two or more of the two or more inflatable balloons of the anchoring cuff at different longitudinal locations along the endotracheal tube. The method may include positioning the two or more inflatable balloons of the anchoring cuff circumferentially surrounding the endotracheal tube. The method may include independently varying pressures under instructions from the controller based on a pre-determined schedule. The method may include independently varying pressures under instructions from the controller based on sensor input that detects tissue inflammation. The method may include independently varying pressures under instructions from the controller based on a scheduled time at a pre-determined pressure. The method may include independently varying pressures under instructions from the controller based on sensor input that detects peristalsis in the esophagus of the subject. The method may include detecting tissue inflammation proximate the endotracheal tube in the subject with a sensor.

The method may include maintaining under instructions from the controller rolling contact of the anchoring cuff with the esophagus and a constant position in the esophagus of the subject. The method may include maintaining, under instructions from the controller, rolling contact of the anchoring cuff including the two or more actively- and independently-controllable inflatable balloons configured to maintain a rolling toroid. The method may include maintaining, under instructions from the controller, rolling contact of the anchoring cuff including the two or more actively- and independently-controllable inflatable balloons configured to maintain three or more azimuthally separated rolling spheres.

A device is disclosed that includes an endotracheal tube having an interior surface and an exterior surface; an actively-controllable anchoring cuff including two or more actively- and independently-controllable inflatable balloons configured to be inflated to differentially varying pressures, wherein the two or more inflatable balloons are configured to contact the exterior surface of the endotracheal tube and configured to contact the trachea of a mammalian subject; and a controller in communication with the pressure sensor, the controller configured to actively vary pressure within one or more of the two or more inflatable balloons of the anchoring cuff. The device may include a pressure sensor configured to detect pressure within one or more of the two or more inflatable balloons.

A method is disclosed that includes detecting insertion of an endotracheal tube including an actively-controllable anchoring cuff comprising two or more inflatable balloons in contact with the exterior surface of the endotracheal tube into a trachea of a mammalian subject; and actively and independently varying pressure of the two or more of the inflatable balloons of the anchoring cuff under instructions from a controller in communication with the pressure sensor. The method may include detecting pressure of one or more of the two or more inflatable balloons with a pressure sensor. The method may include differentially varying pressure of the two or more of the inflatable balloons of the anchoring cuff under instructions from a controller in communication with the pressure sensor.

The method may include applying pressure under instructions from the controller at or above a specified anchor pressure to a first set of two or more of the inflatable balloons. The anchoring cuff may inhibit motion of the endotracheal tube within the trachea. The method may include applying pressure under instructions from the controller below the specified anchor pressure to a second set of the one or more of the inflatable balloons.

A method is disclosed that includes inserting a device including an endotracheal tube having an interior surface and an exterior surface into a trachea of a mammalian subject, wherein the device includes an actively-controllable anchoring cuff including two or more inflatable balloons configured to contact the exterior surface of the endotracheal tube and configured to contact a trachea of a mammalian subject; a pressure sensor configured to detect pressure of the two or more inflatable balloons; and a controller in communication with the pressure sensor, the controller configured to actively vary pressure within one or more of the two or more inflatable balloons of the anchoring cuff.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 2A and 2B depict a diagrammatic view of an aspect of a device including an endotracheal tube.

DETAILED DESCRIPTION

Figure 1A:
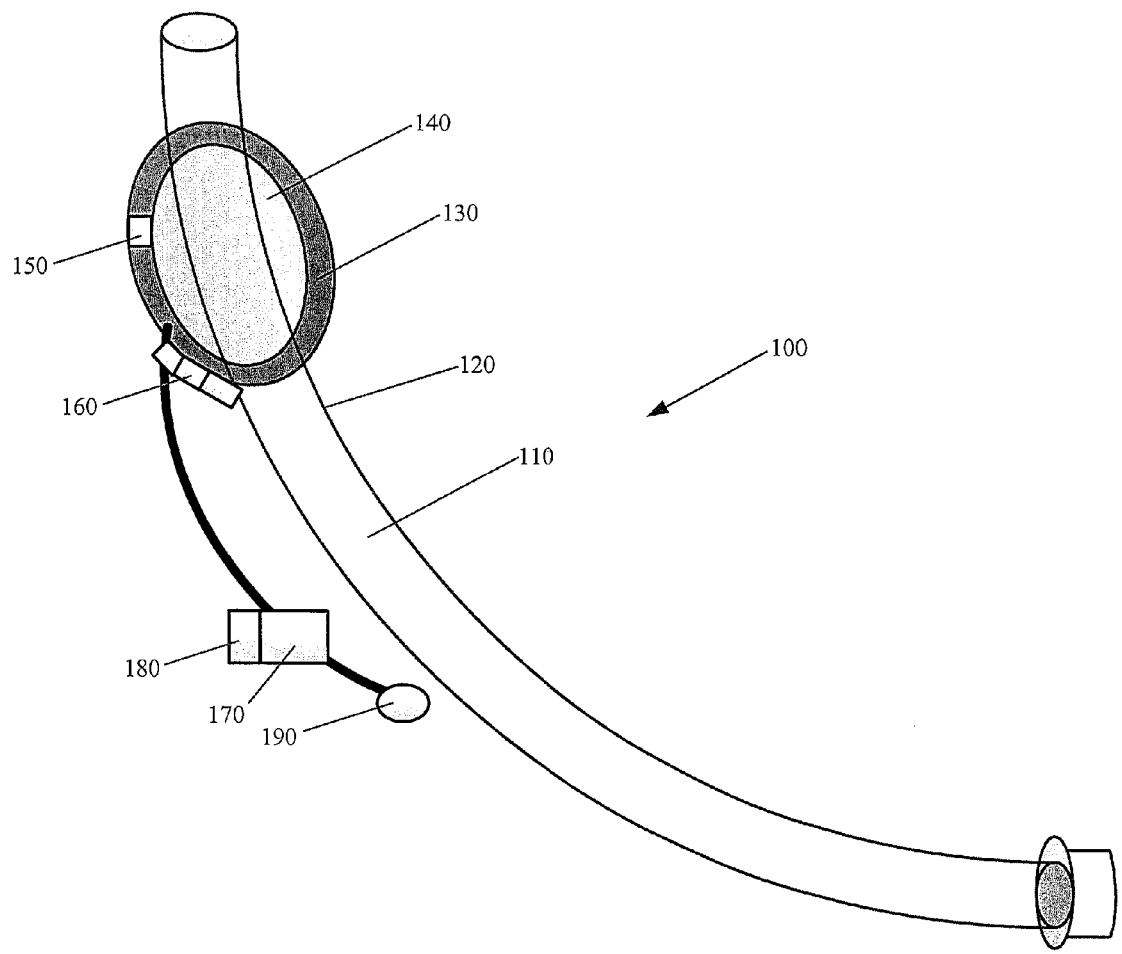
FIGS. 1A and 1B depict a diagrammatic view of an aspect of a device including an endotracheal tube.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Devices and methods are disclosed herein for prevention or treatment of ventilator-assisted pneumonia (VAP) in a subject utilizing an endotracheal tube. The device includes an endotracheal tube (ET) constructed with a cuff and a sealant to seal the endotracheal tube within the trachea to help prevent infections, including ventilator-assisted pneumonia, in a subject using the endotracheal tube. The sealant may include a thermo-responsive sealant surrounding the cuff of the ET. Alternatively, the sealant may include one or more closed cell layers surrounding the cuff of the ET. Alternatively, the sealant may include an actively-controllable anchoring cuff comprising two or more inflatable balloons in contact with the cuff of the ET.

A device is disclosed that includes an endotracheal tube having an interior surface and an exterior surface; a sealant composition in contact with the exterior surface of the endotracheal tube; and a temperature control element in contact with the endotracheal tube configured to heat or cool the sealant composition to a level required to reversibly convert the sealant composition from a solid sealant composition to a flowable sealant composition.

In some embodiments, the temperature control element may be configured to reversibly convert the sealant composition from the solid sealant composition at a temperature below a physiological transition temperature to the flowable sealant composition at a temperature above the physiological transition temperature. In alternative embodiments, the temperature control element may be configured to reversibly convert the sealant composition from the solid sealant composition at a temperature above a physiological transition temperature to the flowable sealant composition at a temperature below the physiological transition temperature.

A method is disclosed that includes inserting an endotracheal tube including a sealant composition in contact with an exterior surface of the endotracheal tube into a trachea of a mammalian subject; and adjusting a temperature control element in contact with the endotracheal tube to heat or cool the endotracheal tube and to reversibly convert the sealant composition between a solid sealant composition and a flowable sealant composition.

In some embodiments, the method includes adjusting the temperature control element in contact with the endotracheal tube to heat or cool the endotracheal tube or the sealant composition to reversibly convert the sealant composition from the solid sealant composition at a temperature below a physiological transition temperature to the flowable sealant composition at a temperature above the physiological transition temperature. In alternative embodiments, the method includes adjusting the temperature control element in contact with the endotracheal tube to heat or cool the endotracheal tube or the sealant composition to reversibly convert the sealant composition from the solid sealant composition at a temperature above a physiological transition temperature to the flowable sealant composition at a temperature below the physiological transition temperature.

A device is disclosed that includes an endotracheal tube having an interior surface and an exterior surface; an actively-controllable anchoring cuff including two or more inflatable balloons configured to contact the exterior surface of the endotracheal tube and configured to contact a trachea of a mammalian subject; a pressure sensor configured to detect pressure of the two or more inflatable balloons; and a controller in communication with the pressure sensor, the controller configured to actively vary pressure within one or more of the two or more inflatable balloons of the anchoring cuff.

A method is disclosed that includes detecting insertion of an endotracheal tube including an actively-controllable anchoring cuff comprising two or more inflatable balloons in contact with an exterior surface of the endotracheal tube into a trachea of a mammalian subject; detecting pressure of one or more of the inflatable balloons with a pressure sensor; and actively varying pressure of the one or more of the inflatable balloons of the anchoring cuff under instructions from a controller in communication with the pressure sensor.

A device is disclosed that includes an endotracheal tube having an interior surface and an exterior surface; an actively-controllable anchoring cuff including two or more actively- and independently-controllable inflatable balloons configured to be inflated to differentially varying pressures, wherein the two or more inflatable balloons are configured to contact the exterior surface of the endotracheal tube and configured to contact the trachea of a mammalian subject; and a controller in communication with the pressure sensor, the controller configured to actively vary pressure within one or more of the two or more inflatable balloons of the anchoring cuff.

A method is disclosed that includes detecting insertion of an endotracheal tube including an actively-controllable anchoring cuff comprising two or more inflatable balloons in contact with the exterior surface of the endotracheal tube into a trachea of a mammalian subject; and actively and independently varying pressure of the two or more of the inflatable balloons of the anchoring cuff under instructions from a controller in communication with the pressure sensor.

A method is disclosed that includes inserting a device including an endotracheal tube having an interior surface and an exterior surface into a trachea of a mammalian subject, wherein the device includes an actively-controllable anchoring cuff including two or more inflatable balloons configured to contact the exterior surface of the endotracheal tube and configured to contact a trachea of a mammalian subject; a pressure sensor configured to detect pressure of the two or more inflatable balloons; and a controller in communication with the pressure sensor, the controller configured to actively vary pressure within one or more of the two or more inflatable balloons of the anchoring cuff.

A device is disclosed that includes an endotracheal tube having an interior surface and an exterior surface; and one or more closed cell layers in contact with the exterior surface and circumferentially surrounding one or more longitudinal portion of the endotracheal tube, wherein the one or more closed cell layers are flexibly shaped to reversibly form a seal in a trachea of a mammalian subject.

A method is disclosed that includes detecting insertion of an endotracheal tube including one or more closed cell layers in contact with an exterior surface of the endotracheal tube into a trachea of a mammalian subject; and adjusting a temperature control element in contact with the endotracheal tube to convert the one or more closed cell layers from non-compressible closed cell layers to compressible closed cell layers.

FIG. 1A depicts a diagrammatic view of an aspect of a device 100 including an endotracheal tube 110. The device includes an endotracheal tube 110 having an interior surface and an exterior surface 120; a sealant composition 130 in contact with the exterior surface of the endotracheal tube 110; and a temperature control element 150 to heat or cool the sealant composition 130 in contact with the endotracheal tube 110. The temperature control element 150 is configured to convert the sealant composition 130 from a solid composition below a physiological transition temperature to a flowable composition at a temperature above the physiological transition temperature, when the sealant composition 130 is in contact with the exterior surface 120 of the endotracheal tube 110. The sealant composition 130 is also in contact with an inflatable cuff 140 on the endotracheal tube 110. The device may include a temperature sensor 160 configured to measure the temperature of one or more of the sealant composition 130 and the endotracheal tube 110. The device may include a reservoir 170 including a pump 180 in fluidic communication with the exterior surface of the endotracheal tube and configured to contain the sealant composition and to pump the sealant composition 130 to contact the exterior surface 120 of the endotracheal tube 110. The device may include a controller 190 configured to regulate the temperature control element 150 and reservoir pump 180 in response to a temperature measurement from the temperature sensor 150. The expanded sealant composition 130 may fill the space of the trachea of the subject to prevent infectious agents from moving through the respiratory system of the subject. The contracted sealant composition 130 allows the endotracheal tube to be removed from the trachea of the subject.

Figure 1B:
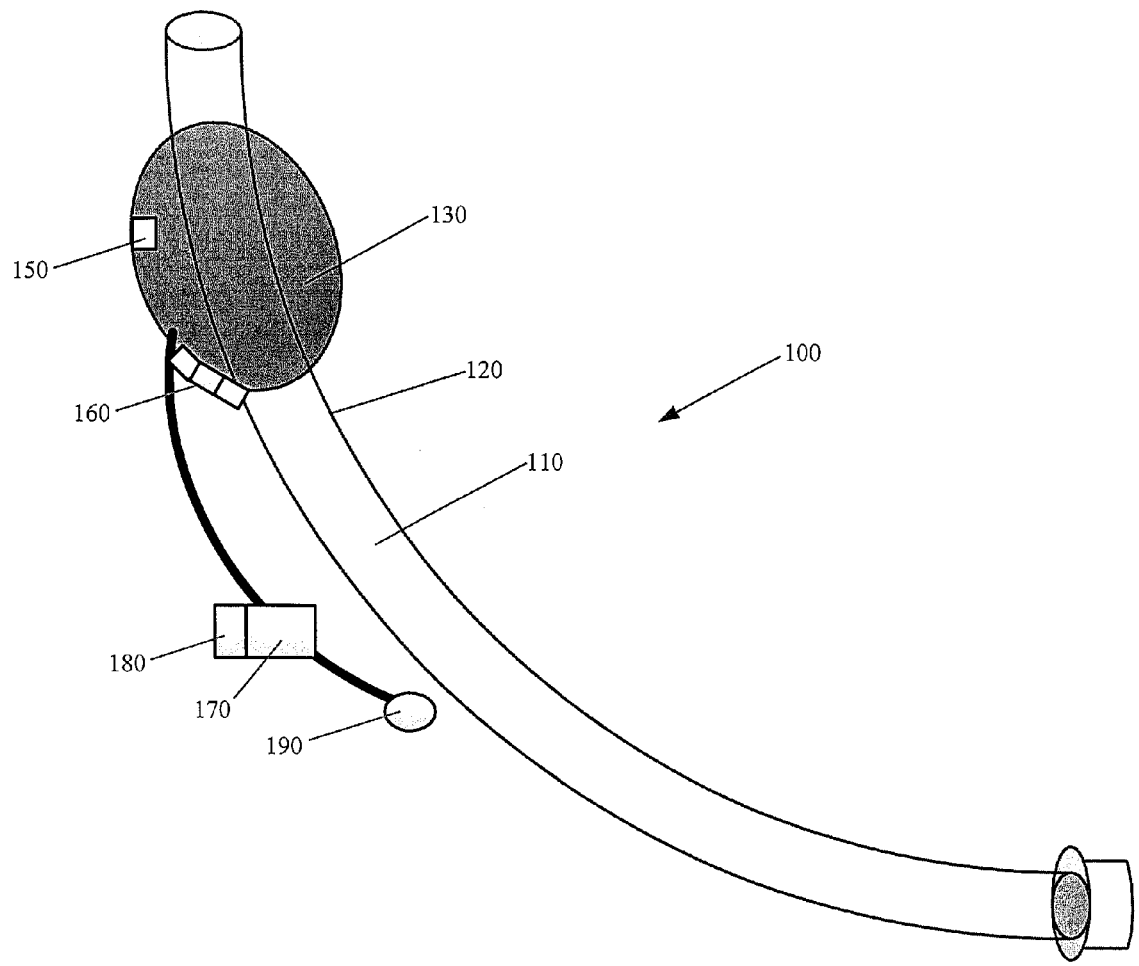

FIG. 1B depicts a diagrammatic view of an aspect of a device 100 including an endotracheal tube 110. The device includes an endotracheal tube 110 having an interior surface and an exterior surface 120; a sealant composition 130 in contact with the exterior surface of the endotracheal tube 110; and a temperature control element 150 to heat or cool the sealant composition 130 in contact with the endotracheal tube 110. The temperature control element 150 is configured to convert the sealant composition 130 from a solid composition below a physiological transition temperature to a flowable composition at a temperature above the physiological transition temperature, when the sealant composition 130 is in contact with the exterior surface 120 of the endotracheal tube 110. The device may include a temperature sensor 160 configured to measure the temperature of one or more of the sealant composition 130 and the endotracheal tube 110. The device may include a reservoir 170 including a pump 180 in fluidic communication with the exterior surface of the endotracheal tube and configured to contain the sealant composition and to pump the sealant composition 130 to contact the exterior surface 120 of the endotracheal tube 110. The device may include a controller 190 configured to regulate the temperature control element 150 and reservoir pump 180 in response to a temperature measurement from the temperature sensor 150.

Figure 2A:
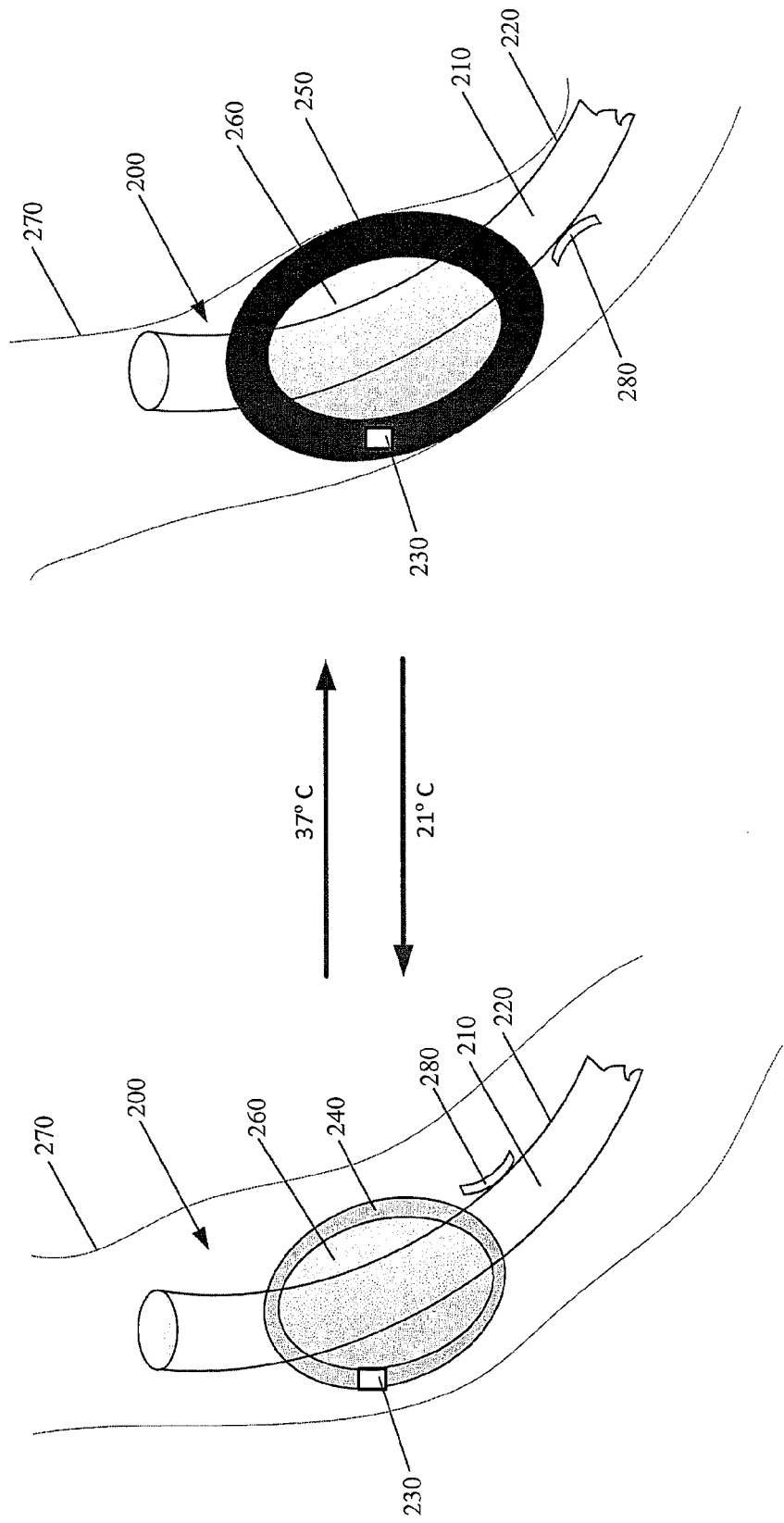

FIG. 2A depicts a diagrammatic view of an aspect of a device 200 including an endotracheal tube 210 within a trachea 270 of a subject. The device includes an endotracheal tube 210 having an interior surface and an exterior surface 220; a sealant composition 240, 250 in contact with the exterior surface 220 of the endotracheal tube 210; and a temperature control element 230 to heat or cool the sealant composition 240 in contact with the endotracheal tube 210. The temperature control element 230 is configured to convert the sealant composition 240, 250 from a flowable composition 240 below a physiological transition temperature to a solid composition 250 at a temperature above the physiological transition temperature, when the sealant composition 240 is in contact with the exterior surface 220 of the endotracheal tube 210. The sealant composition 240 may be in contact with an exterior surface of an inflatable cuff 260 on the endotracheal tube 210. The expanded solid sealant composition 250 may fill the space of the trachea of the subject to prevent infectious agents from moving through the respiratory system of the subject. The contracted flowable sealant composition 240 allows the endotracheal tube to be removed from the trachea of the subject. The device may include a sensor 280 configured to detect inflammation of tissue proximate the endotracheal tube 210.

FIG. 2B depicts a diagrammatic view of an aspect of a device 200 including an endotracheal tube 210 within a trachea 270 of a subject. The device includes an endotracheal tube 210 having an interior surface and an exterior surface 220; a sealant composition 240, 250 in contact with the exterior surface 220 of the endotracheal tube 210; and a temperature control element 230 to heat or cool a sealant composition 240, 250 in contact with the endotracheal tube 210 configured to convert the sealant composition 240, 250 from a flowable composition 240 below a physiological transition temperature to a solid composition 250 at a temperature above the physiological transition temperature, when the sealant composition 240, 250 is in contact with the exterior surface 220 of the endotracheal tube 210. The expanded solid sealant composition 250 may fill the space of the trachea of the subject to prevent infectious agents from moving through the respiratory system of the subject. The contracted flowable sealant composition 240 allows the endotracheal tube to be removed from the trachea of the subject. The device may include a sensor 280 configured to detect inflammation of tissue proximate the endotracheal tube 210.

Figure 3A:
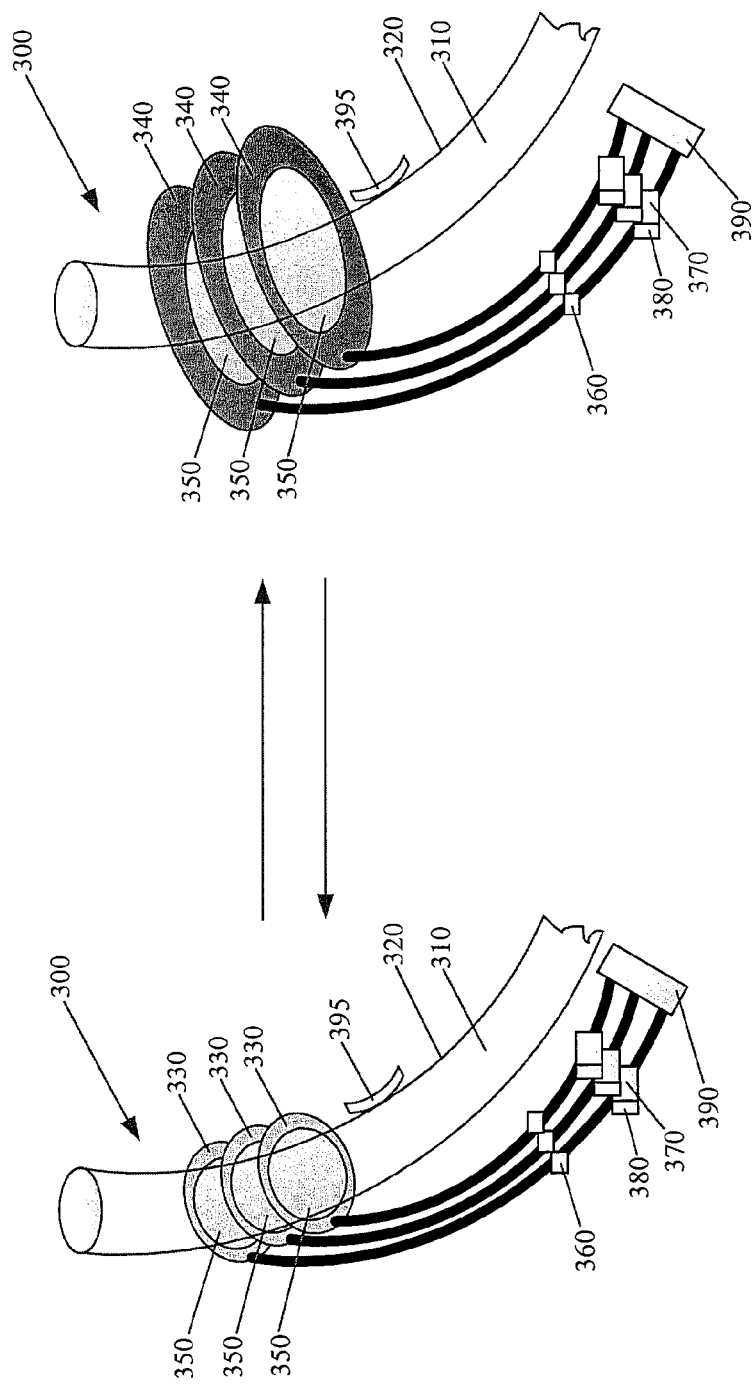
FIGS. 3A and 3B depict a diagrammatic view of an aspect of a device including an endotracheal tube.

FIG. 3A depicts a diagrammatic view of an aspect of a device 300 including an endotracheal tube 310. The device includes an endotracheal tube 310 having an interior surface and an exterior surface 320; and a sealant composition including one or more closed cell foam layers 330, 340 in contact with the exterior surface 320 of the endotracheal tube 310 wherein the one or more closed cell foam layers 330, 340 are circumferentially surrounding one or more longitudinal portion of the endotracheal tube 310, wherein the closed cell foam layer 330, 340 is configured to reversibly form a seal in a trachea of a mammalian subject. The closed cell foam layer may be, for example, a compressible foam or a shape memory material capable of forming alternative shapes to be a contracted closed cell foam layer 330 or an expanded closed cell foam layer 340. The expanded closed cell foam layer 340 may fill the space of the trachea of the subject to prevent infectious agents from moving through the respiratory system of the subject. The contracted closed cell foam layer 330 allows the endotracheal tube to be removed from the trachea of the subject. The sealant composition 330, 340 may be in contact with an exterior surface of an inflatable cuff or inflatable balloon 350 on the endotracheal tube 310 and may be in contact with the exterior surface 320 of the endotracheal tube 310. The device may include a reservoir 370 and a reservoir pump 380 in fluidic communication with the contracted closed cell foam layer 330 and the exterior surface 320 of the endotracheal tube 310. The reservoir 370 is configured to contain the sealant composition as the contracted closed cell foam layer 330 and to pump the contracted closed cell foam layer 330 to contact the exterior surface 320 of the endotracheal tube 310. The device may include a controller 390 configured to regulate a pressure sensor 360 and reservoir pump 380 in response to a pressure measurement of the sealant composition against the trachea of the subject from the pressure sensor 360. The controller 390 may actively control the one or more closed cell foam layers 330, 340 and may independently vary an amount of the one or more closed cell foam layers 330, 340 or the pressure exerted by the one or more closed cell foam layers 330, 340 on the trachea of the subject. The device may include a sensor 395 configured to detect inflammation of tissue proximate the endotracheal tube 310.

Figure 3B:
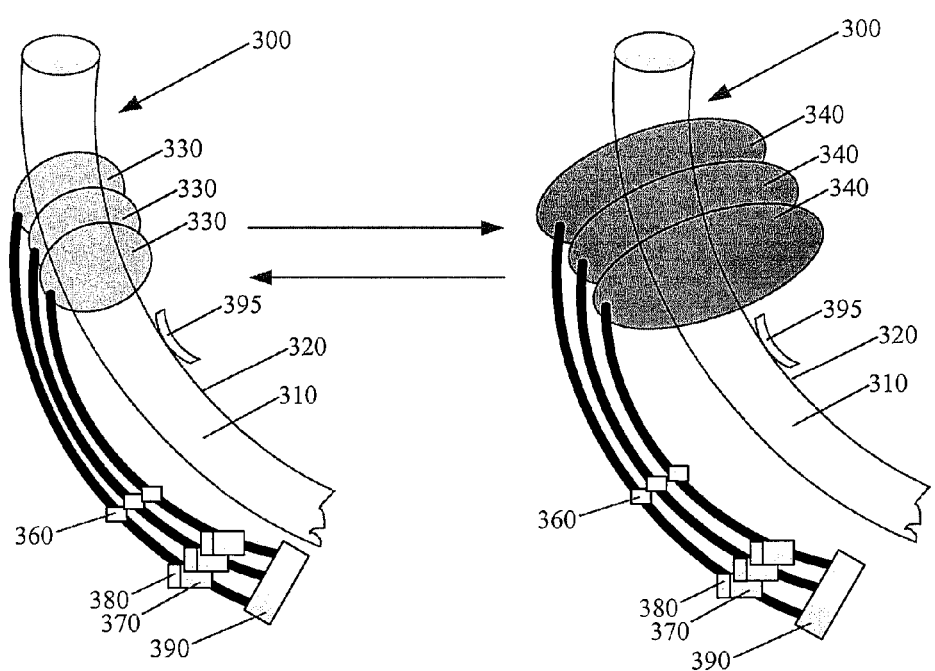

FIG. 3B depicts a diagrammatic view of an aspect of a device 300 including an endotracheal tube 310. The device includes an endotracheal tube 310 having an interior surface and an exterior surface 320; and a sealant composition including one or more closed cell foam layers 330, 340 in contact with the exterior surface 320 of the endotracheal tube 310 wherein the one or more closed cell foam layers 330, 340 are circumferentially surrounding one or more longitudinal portion of the endotracheal tube 310, wherein the closed cell foam layer 330, 340 is configured to reversibly form a seal in a trachea of a mammalian subject. The closed cell foam layer 330, 340 may be, for example, a compressible foam or a shape memory material. The expanded closed cell foam layer 340 may fill the space of the trachea of the subject to prevent infectious agents from moving through the respiratory system of the subject. The contracted closed cell foam layer 330 allows the endotracheal tube to be removed from the trachea of the subject. The sealant composition 330, 340 may be in contact with the exterior surface 320 of the endotracheal tube 310. The device may include a reservoir 370 and a reservoir pump 380 in fluidic communication with the exterior surface 320 of the endotracheal tube 310. The reservoir 370 is configured to contain the sealant composition as the contracted closed cell foam layer 330 and to pump the contracted closed cell foam layer 330, to contact the exterior surface 320 of the endotracheal tube 310. The device may include a controller 390 configured to regulate a pressure sensor 360 and reservoir pump 380 in response to a pressure measurement of the sealant composition against the trachea of the subject from the pressure sensor 360. The controller 390 may actively control the one or more closed cell foam layers 330, 340 and may independently vary an amount of the one or more closed cell foam layers 330, 340 or the pressure exerted by the one or more closed cell foam layers 330, 340 on the trachea of the subject. The device may include a sensor 395 configured to detect inflammation of tissue proximate the endotracheal tube 310.

Figure 4:
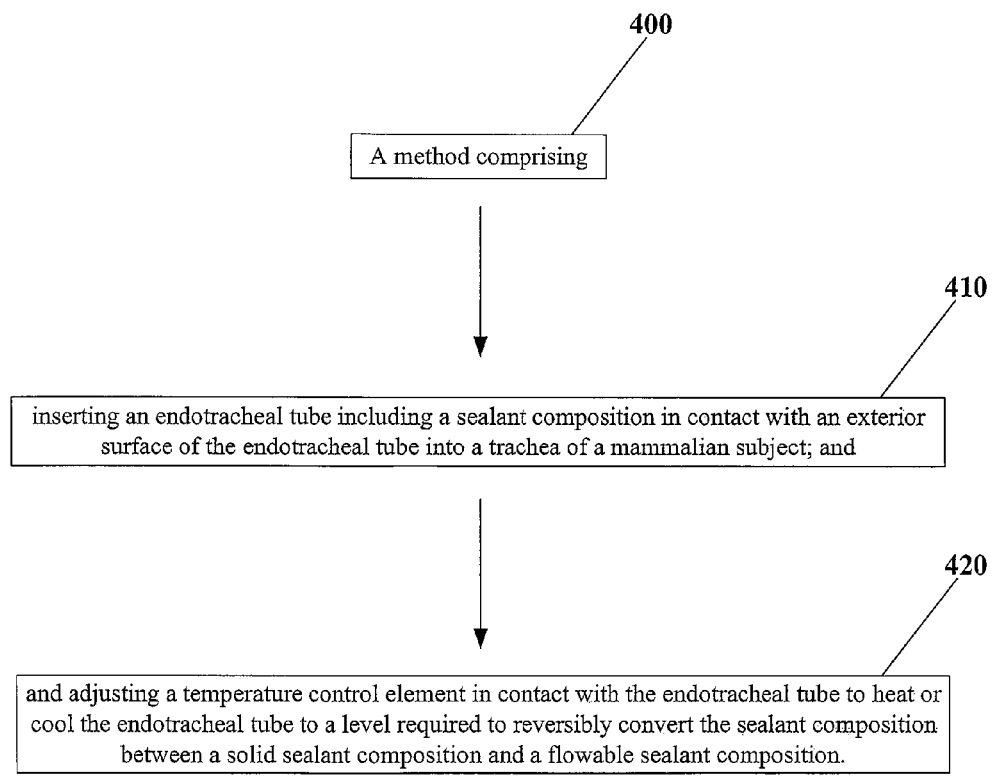
FIG. 4 is a diagrammatic view of an aspect of a method that includes inserting an endotracheal tube into a trachea of a mammalian subject.

FIG. 4 depicts a diagrammatic view of a method 400 that includes inserting 410 an endotracheal tube including a sealant composition in contact with an exterior surface of the endotracheal tube into a trachea of a mammalian subject; and adjusting 420 a temperature control element in contact with the endotracheal tube to heat or cool the endotracheal tube and to reversibly convert the sealant composition between a solid sealant composition and a flowable sealant composition.

Figure 5:
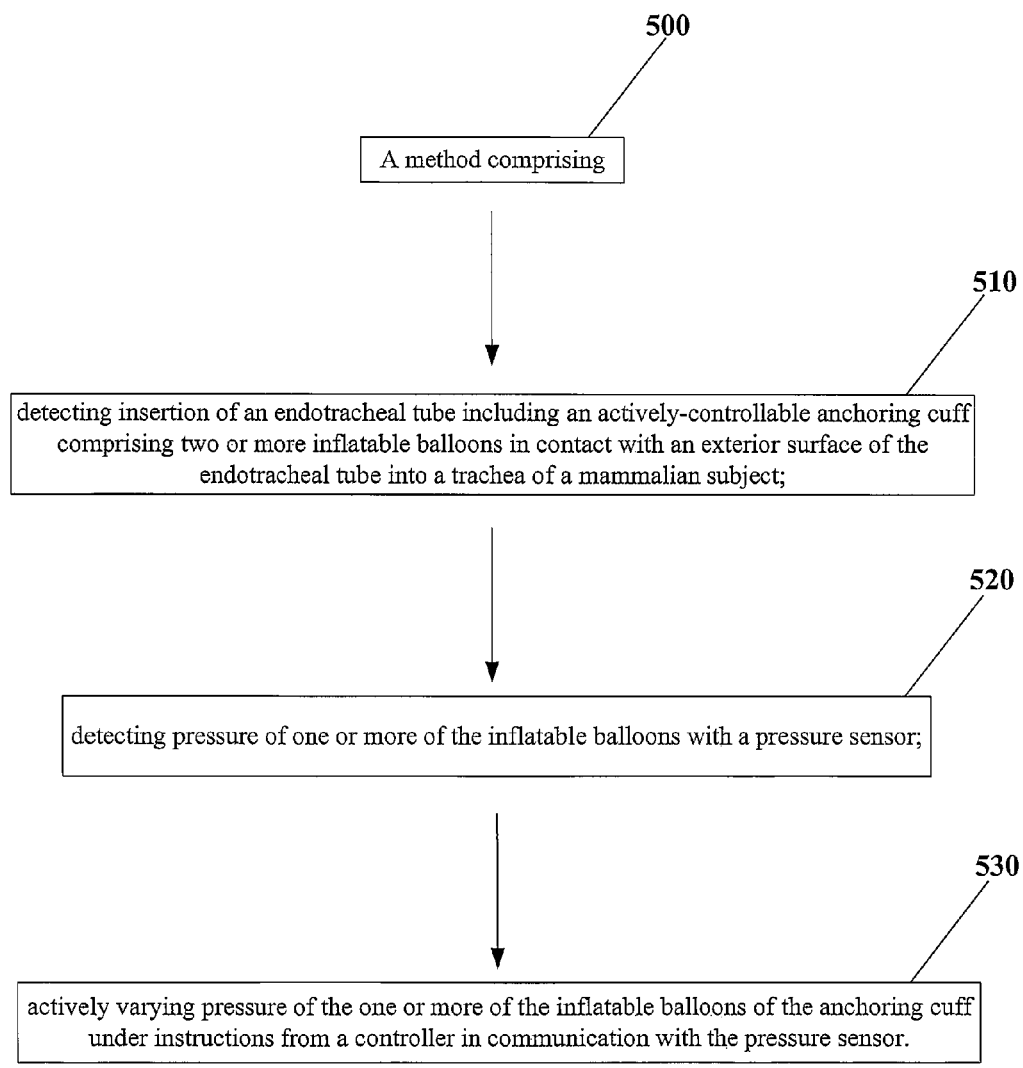
FIG. 5 is a diagrammatic view of an aspect of a method that includes inserting an endotracheal tube into a trachea of a mammalian subject.

FIG. 5 depicts a diagrammatic view of a method 500 that includes detecting insertion of 510 an endotracheal tube including an actively-controllable anchoring cuff comprising two or more inflatable balloons in contact with an exterior surface of the endotracheal tube into a trachea of a mammalian subject; detecting 520 pressure of one or more of the inflatable balloons with a pressure sensor; and actively varying 530 pressure of the one or more of the inflatable balloons of the anchoring cuff under instructions from a controller in communication with the pressure sensor.

Figure 6:
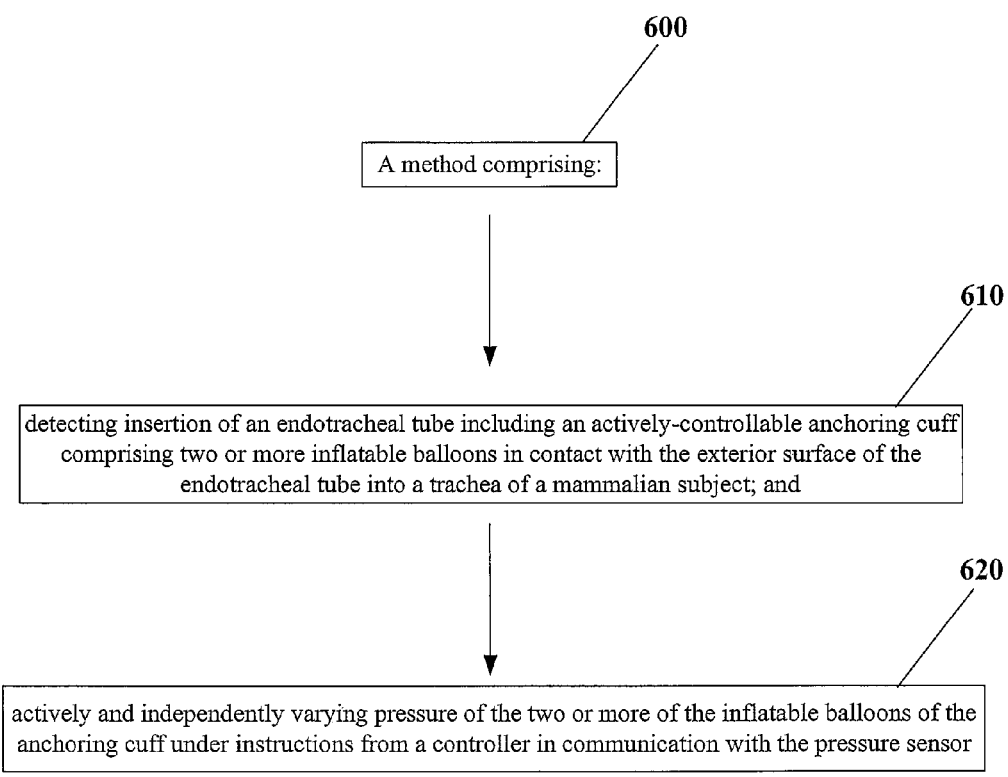
FIG. 6 is a diagrammatic view of an aspect of a method that includes inserting an endotracheal tube into a trachea of a mammalian subject.

FIG. 6 depicts a diagrammatic view of a method 600 that includes detecting insertion of 610 an endotracheal tube including an actively-controllable anchoring cuff comprising two or more inflatable balloons in contact with the exterior surface of the endotracheal tube into a trachea of a mammalian subject; and actively and independently varying 620 pressure of the two or more of the inflatable balloons of the anchoring cuff under instructions from a controller in communication with the pressure sensor.

Figure 7:
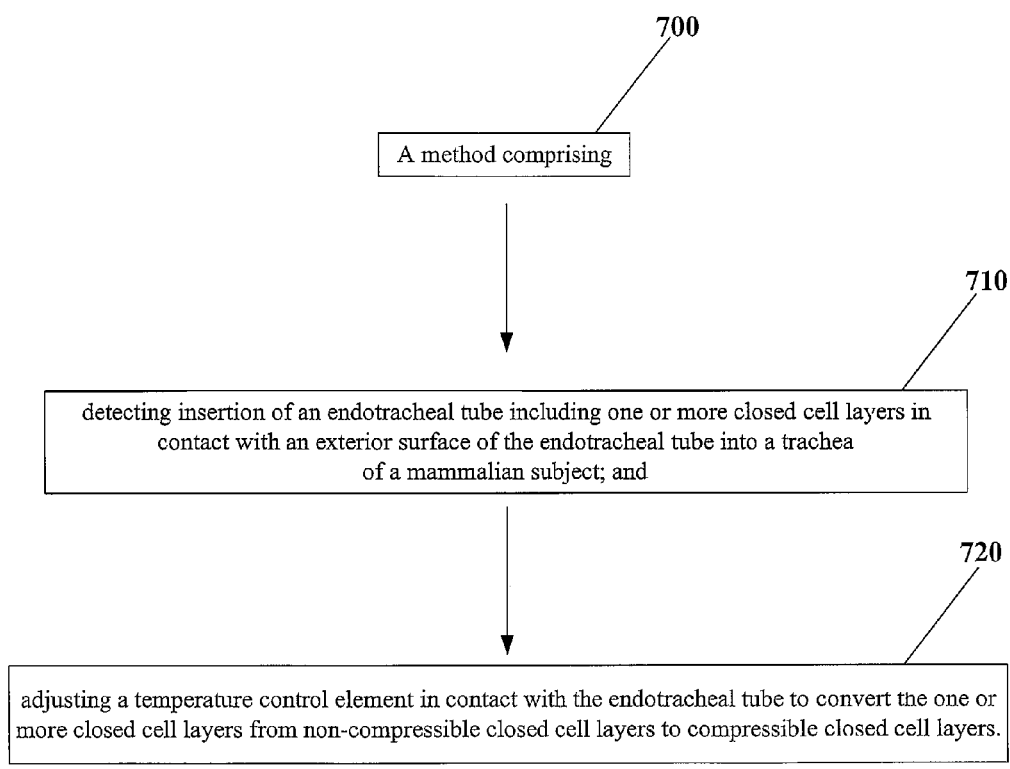
FIG. 7 is a diagrammatic view of an aspect of a method that includes inserting an endotracheal tube into a trachea of a mammalian subject.

FIG. 7 depicts a diagrammatic view of a method 700 that includes inserting 710 an endotracheal tube including one or more closed cell layers in contact with an exterior surface of the endotracheal tube into a trachea of a mammalian subject; and adjusting 720 a temperature control element in contact with the endotracheal tube to convert the one or more closed cell layers from non-compressible closed cell layers to compressible closed cell layers.

Thermoresponsive Polymer as Sealant Composition for Endotracheal Tube.

An endotracheal tube may be fabricated with an airway tube and a spherical inflatable cuff for oral or nasal intubations into a mammalian subject. See, e.g., specification sheet: Mallinckrodt™ Hi-Lo endotracheal tube available from Covidien Corp., Mansfield, Mass., which is incorporated herein by reference. The airway tube diameter may be adjusted to meet the size of the trachea of the mammalian subject. In some aspects, the airway tube may be approximately 7.5 mm inside diameter. The inflatable cuff of the endotracheal tube is manufactured with a sealant composition that is a thermo-responsive sealant surrounding the cuff. The sealant composition is a thermally-responsive polymer which transitions from a flowable phase to a solid phase at temperatures close to body temperature, approximately 37° C., of the subject. In some aspects, the sealant composition may convert from a solid composition at or below a physiological transition temperature, e.g., 37° C., to a flowable composition at a temperature, e.g., 39° C., above the physiological transition temperature in response to a heating element in contact with the endotracheal tube. Alternatively, the sealant composition may be a thermally-responsive polymer that transitions from a flowable phase to a solid phase at or above temperatures close to body temperature of the subject, e.g., a flowable to solid phase transition at approximately 37° C. For example, a polymer of N-isopropylacrylamide (NIPAAm) has a phase transition temperature of approximately 37° C. At temperatures below 37° C. NIPAAm polymer is flowable and after entering the body and heating to 37° C. the polymer transitions to a gel. See e.g., U.S. Pat. No. 7,985,601 issued to Healy et al. on Jul. 26, 2011, which is incorporated herein by reference.

The sealant composition includes a cross-linked network that is synthesized using a thermo-responsive polymer, such as poly(N-isopropylacrylamide) [p(NIPAAm)]. In addition, linear polymer chains, entangled within the thermo-responsive matrix may be functionalized with one or more bioactive molecules, for example, one or more antimicrobial drugs. The linear polymer chains can be any macromolecule that is amenable to conjugation, e.g., containing —COOH, —SH, and —NH$_2$ functional groups, with the bioactive molecules and does not affect the phase behavior of the thermo-responsive matrix, e.g., lower critical solution temperature and volume change. Thus, in a first aspect, the sealant composition includes: (a) a cross-linked thermo-responsive polymer; and (b) a linear polymer entangled within said cross-linked thermo-responsive polymer, said linear polymer derivatized with a bioactive molecule. The crosslinked sealant composition is extremely pliable and fluid-like at room temperature (RT), but demonstrate a phase transition as the matrix warms from RT to body temperature, yielding more rigid structures. Thus, the sealant composition offers the benefit of in situ stabilization without the potential adverse effects of in situ polymerization (e.g., residual monomers, initiators, catalysts, etc.).

The sealant composition is tunable in terms of delivery, drug dosing, and mechanical and biochemical properties. The sealant composition is preferably deployed by minimally invasive methods, so at room temperature (i.e., approximately equal to 20-27° C.) the loosely-crosslinked networks are flowable, i.e., injectable through a small diameter aperture (from about 1 mm in diameter to about 5 mm in diameter) and do not exhibit macroscopic fracture following injection.

In some aspects, the thermo-responsive polymer-based hydrogels are synthesized by simultaneously polymerizing and cross-linking N-isopropylacrylamide (NIPAAm) and acrylic acid (AAc) [p(NIPAAm-co-AAc) hydrogels]. To synthesize the sealant composition, the methods may be modified by adding linear p(AAc) chains during the hydrogel formation. Due to the presence of the p(NIPAAm), the sealant composition demonstrates a significant increase in complex modulus (i.e., rigidity) when heated to body temperature, without exhibiting a significant change in either volume or water content. In some embodiments, the phase transition of p(NIPAAm) is exploited as a means for minimally invasive delivery of macromolecules, or drugs, e.g., antibiotics, in a site-directed manner to the trachea of a subject.

Polymer Ratios of Thermoresponsive Polymer as Sealant Composition.

The properties of the sealant composition are readily varied by altering the composition of the sealant composition. The mechanical properties of the matrix can be readily altered by the addition of increased cross-links, by varying the NIPAAm:AAc molar ratio in the p(NIPAAm-co-AAc) hydrogel, or by varying the mass of the linear polymer in the sealant composition. Furthermore, the sealant composition fabrication is modular, in that functionalization of the linear polymer chains takes place prior to the sealant composition synthesis, thereby allowing purification and the ability to create admixtures of distinct "macromolecular building blocks."

The structure of the polymerizable thermo-responsive monomer and the amount and structure of the cross-linking agent in the thermo-responsive polymer can be varied to alter the properties of the thermo-responsive polymer matrix. For example, the hydrophobicity/hydrophilicity ratio of the matrix can be varied by altering the hydrophobicity and hydrophilicity of the polymerizable monomers. The properties of the thermoresponsive polymer can be varied by choice of monomer(s), cross-linking agent and degree of polymer cross-linking. An exemplary variation in the monomer properties is hydrophobicity/hydrophilicity.

In general, providing larger hydrophobic moieties on a thermo-responsive polymer decreases water swellability. For example, hydrogels made of isopropyl acrylamide are water swellable and possess small hydrophobic moieties (i.e., an isopropyl group). The hydrophobic binding character of these gels is salt dependent. However, when the isopropyl group is replaced by a larger hydrophobic moiety, e.g., an octyl group, the gel loses some of its water swellability.

Exemplary hydrophilic moieties are derived from monomers that include, but are not limited to, N-methacryloyl-tris(hydroxymethyl)methylamine, hydroxyethyl acrylamide, hydroxypropyl methacrylamide, N-acrylamido-1-deoxysorbitol, hydroxyethylmethacrylate, hydroxypropylacrylate, hydroxyphenylmethacrylate, poly(ethylene glycol) monomethacrylate, poly(ethylene glycol)dimethacrylate, acrylamide, glycerol monomethacrylate, 2-hydroxypropyl acrylate, 4-hydroxybutyl methacrylate, 2-methacryloxyethyl glucoside, poly(ethyleneglycol)monomethyl ether monomethacrylate, vinyl 4-hydroxybutyl ether, and derivatives thereof. In some embodiments, hydrophilic moieties are derived from monomers that include a poly(oxyalkylene) group within their structure or poly(ethylene glycol)-containing monomers.

In some embodiments, hydrophobic moieties are derived from acrylamide monomers in which the amine nitrogen of the amide group is substituted with one or more alkyl residues. For example, hydrophobic moieties are derived from monomers selected from N-isopropylacrylamide, N,N-dimethylacrylamide, N,N-diethyl(meth)acrylamide, N-methyl methacrylamide, N-ethylmethacrylamide, N-propylacrylamide, N-butylacrylamide, N-octyl(meth)acrylamide, N-dodecylmethacrylamide, N-octadecylacrylamide, propyl(meth)acrylate, decyl(meth)acrylate, stearyl(meth)acrylate, octyl-triphenylmethylacrylamide, butyl-triphenylmethylacrylamide, octadedcyl-triphenylmethylacrylamide, phenyl-triphenylmethylacrlamide, benzyl-triphenylmethylacrylamide, and derivatives thereof.

Similar to the thermo-responsive polymer, the hydrophobicity/hydrophilicity of the linear polymer can be varied. Moreover, characteristics of the polymer such as length and number and identity of reactive functional groups can be varied as desired for a particular application. Linear polymer chains may include any long-chain polymer that contains a functional group (e.g., $—NH_2$, $—COO^-$, $—SH$) that is amenable to modification with biomolecules, for example, antibiotics. Examples of such linear polymers include, but are not limited to, hyaluronic acid (HA), poly(methacrylic acid), poly(ethylene glycol)(EG), or poly(lysine). The linear polymer chain may also be a copolymer, e.g., p(AAc-co-EG) or a terpolymer. The linear chain may be amenable to either grafting biological molecules or particles and will not interfere with the phase change properties of the cross-linked network.

In addition to linear polymers, branched polymers, such as commercially available poly(EG) derivatives (e.g., Shearwater Polymers, Huntsville, Ala.), may also be used.

Antimicrobial drugs which may be incorporated into the sealant composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amantadine. See e.g., U.S. Pat. No. 7,985,601, which is incorporated herein by reference.

The sealant composition may comprise a block copolymer with reverse thermal gelation properties. The block copolymer may comprise p(NIPAAm-co-AAc) hydrogel polymer. The block copolymer may further comprise a polyoxyethylene-polyoxypropylene block copolymer such as a biodegradable, biocompatible copolymer of polyethylene oxide and polypropylene oxide. The sealant composition may include a therapeutic agent, e.g., one or more antimicrobial drugs. The device may include a temperature control element to heat or cool the sealant composition in contact with the endotracheal tube. The temperature control element configured to convert the sealant composition as a block copolymer, e.g., p(NIPAAm-co-AAc) hydrogel polymer or polyoxyethylene-polyoxypropylene block copolymer, from a solid composition at a temperature above a physiological transition temperature, e.g., above 37° C., to a flowable composition below a physiological transition temperature, e.g., below 37° C., when the sealant composition is in contact with the exterior surface of the endotracheal tube.

The method for producing the sealant composition may include injecting a first material, which includes a cross-linkable polymer in a flowable form, from a reservoir of the device to contact an exterior surface of an endotracheal tube. The method also includes contacting the first material with a second material from the reservoir. The second material includes a crosslinking agent, and the first material and second material, upon contact, form the sealant composition as a gel on the exterior surface of the endotracheal tube. The method also includes stabilizing the endotracheal tube in a trachea of the subject's body by enabling the sealant composition on the exterior surface to contact the trachea of the subject.

In some embodiments, the sealant composition is formed by contacting a first material with a second material. The first material includes one or more of an anionic crosslinkable polymer, a cationic crosslinkable polymer, or a non-ionically crosslinkable polymer. In other embodiments, the first material includes one or more of poly acrylic acids, polymethacrylic acid, alginic acid, pectinic acids, sodium alginate, potassium alginate, carboxy methyl cellulose, hyaluronic acid, heparin, carboxymethyl starch, carboxymethyl dextran, heparin sulfate, chondroitin sulfate, polyethylene amine, polysaccharides, chitosan, carboxymethyl chitosan, cationic starch or salts thereof.

In some embodiments, the second material includes one or more of an anionic crosslinking ion, a cationic crosslinking ion, or a non-ionic crosslinking agent. In other embodiments of the method, the second material includes one or more of phosphate, citrate, borate, succinate, maleate, adipate, oxalate, calcium, magnesium, barium, strontium, boron, beryllium, aluminum, iron, copper, cobalt, lead, or silver ions. In still other embodiments, the second material includes one or more of divinylsulfone, polycarboxylic acids, polycarboxylic anhydrides, polyamines, epihalohydrins, diepoxides, dialdehydes, diols, carboxylic acid halides, ketenes, polyfunctional aziridines, polyfunctional carbodiimides, polyisocyanate, glutaraldehyde, or polyfunctional crosslinkers including functional groups capable of reacting with organic acid groups.

In some embodiments, the method for producing the sealant composition may further include contacting the gel with a third material that includes a de-crosslinking agent. In some embodiments, the third material includes one or more of sodium phosphate, sodium citrate, inorganic sulfates, ethylene diamine tetraacetic acid and ethylene dimethyl tetraacetate, citrates, organic phosphates (e.g., cellulose phosphate), inorganic phosphates (e.g., pentasodium tripolyphosphate, mono- and di-basic potassium phosphate, sodium pyrophosphate), phosphoric acid, trisodium carboxymethyloxy succinate, nitrilotriacetic acid, maleic acid, oxalate, polyacrylic acid, sodium, potassium, calcium, or magnesium ions.

The sealant composition possesses a transition temperature, which is the temperature at which the sealant composition transition from liquid to gel form. Suitable sealant composition includes polyoxyethylene-polyoxypropylene (PEO-PPO) block copolymers. Two acceptable compounds are Pluronic® acid F127 and F108 nonionic, surfactant polyol. Pluronic® acid F127 and F108 are PEO-PPO block copolymers with molecular weights of 12,600 and 14,600, respectively. Each of these compounds is available from BASF of Mount Olive, N.J. Pluronic® acid F108 at 20-28% concentration in phosphate buffered saline (PBS) is an example of a suitable sealant composition. A suitable sealant composition preparation of 22.5% Pluronic® acid F108 in PBS has a transition temperature from liquid to gel of 37° C. Pluronic® acid F127 at 20-35% concentration in PBS is another example of a suitable sealant composition. A preparation of 20% Pluronic® acid F127 in PBS has a transition temperature from liquid to gel of 37° C. Low concentrations of dye (such as crystal violet), hormones, therapeutic agents, fillers, and antibiotics may be added to the sealant composition. For example, one or more antimicrobial drugs may be carried by the sealant composition and thus delivered to the trachea of the subject via the sealant composition. In general, other PEO-PPO block copolymers as sealant compositions that are biocompatible, biodegradable, and exist as a gel at body temperature and a liquid at below body temperature may also be used. The molecular weight of a suitable material (such as a block copolymer) may be, for example, between 5,000 and 25,000, and more particularly between 7,000 and 15,000, and, for the two specific compounds identified above, 12,600 or 14,600.

Sealant compositions that include crosslinkable polymers may transition to a gel state when contacted with a crosslinking agent. In some embodiments, the sealant composition may be injected as one or more crosslinkable polymers surrounding the endotracheal tube and may contact the crosslinkable polymers with one or more crosslinking agents. The combination of crosslinkable polymers with one or more crosslinking agents enables the sealant composition in a gel state to contact an exterior surface of the endotracheal tube and the trachea of the subject. The crosslinkable polymer(s) may contact the crosslinking agent(s) before or after injection to contact an exterior surface of the endotracheal tube and the trachea of the subject. If the crosslinkable polymer(s) contact the crosslinking agent(s) before injection to contact an exterior surface of the endotracheal tube, then mixture of crosslinkable polymer(s) and crosslinking agent(s) should be injected prior to the crosslinking reaction occurring and the transformation of the materials into gel form. Contacting the gel formed with crosslinkable polymer(s) with a de-crosslinking agent dissolves the gel and facilitates its removal. Once the gel is dissolved, it can be removed when the endotracheal tube is removed from the subject. Alternatively, the dissolved gel flows through the digestive tract of the body and is expelled from the body with the urine. The gel may also be removed by extraction of the material through a catheter or a percutaneous access device such as a needle. See e.g., U.S. Pat. No. 8,394,059 issued to Sahatjian et al. on Mar. 12, 2013, which is incorporated herein by reference.

In other aspects, the sealant composition may be a wax polymer that includes highly branched polymers having a combination of high molecular weight and low melting points. The device may include a temperature control element to heat or cool the sealant composition in contact with the endotracheal tube. The temperature control element configured to convert the sealant composition as a wax polymer from a solid composition at a temperature below the physiological transition temperature, e.g., below 37° C., to a flowable composition above a physiological transition temperature, e.g., above 37° C., when the sealant composition is in contact with the exterior surface of the endotracheal tube. The wax polymer, e.g., ISO-Polymers, have gel forming characteristics and may form continuous films. ISO-P 100 HV is a copolymer of poly(C20-28 Olefin) and poly(C30-45 Olefin) that has a melting point of approximately 37.2° C. and a needle penetration ASTM 1321 @ 25° C. of 30 mm depth. The wax polymer has a network of crystalline chains in formulations that enhance stability and control syneresis. See, e.g., International Group Inc. (IGI), Toronto, Ontario, which is incorporated herein by reference.

Endotracheal tubes that include inflatable cuffs may be constructed of polyurethane with a thickness of approximately 7 μm. An endotracheal tube may include an ultrathin polyurethane cuff to reduce channel formation and fluid leakage from the subglottic area. See e.g., Lorente et al., *Am. J. Respir. Care Med.* 176: 1079-1083, 2007, which is incorporated herein by reference.

Shape Memory Polymer as Sealant Composition.

The endotracheal tube may include a sealant composition that includes a closed cell foam material. The closed cell foam may include biodegradable shape-memory polymers. Biodegradable shape-memory polymers form one or more layers in contact with the exterior surface of the endotracheal tube wherein the one or more layers of shape-memory polymer are circumferentially surrounding one or more longitudinal portion of the endotracheal tube. The shape-memory polymer layer is configured with the endotracheal tube to reversibly form a seal in a trachea of a mammalian subject. To control the shape-memory polymer functioning as a sealant composition, the switching temperature $T_{sw}$, is within specific temperature limits. For example, $T_{sw}$ may be either between room temperature 20° C. and body temperature 37° C. for automatically inducing the shape change upon implantation. Alternatively, the switching temperature $T_{sw}$ may be slightly above body temperature 37° C. for on demand activation by a sensor and controller function of the implanted device. $T_{sw}$ of amorphous polymer networks from star-shaped rac-dilactide-based macrotetrols and a diisocyanate may be controlled systematically by incorporation of p-dioxanone, diglycolide, or ε-caprolactone as comonomer. Thermomechanical results indicate that $T_{sw}$ may be adjusted between 14° C. and 56° C. by selection of comonomer type and ratio without affecting the advantageous elastic properties of the polymer networks. Furthermore, the hydrolytic degradation rate may be varied in a wide range by the content of easily hydrolyzable ester bonds, the material's hydrophilicity, and its molecular mobility. See e.g., Lendlein et al., *Biomacromolecules* 10: 975-982, 2009, which is incorporated herein by reference.

The endotracheal tube may include a sealant composition that includes biodegradable shape-memory polymers circumferentially surrounding the endotracheal tube. The properties of the shape-memory polymers (SMP) as sealant composition may be controlled by changing the formulation of the polymers, or by changing the treatment of the polymers through polymerization and/or handling after polymerization.

The shape-memory polymer (SMP) as sealant composition may be formed from a first monomer and a second crosslinking monomer. The weight percentages of the first monomer and second monomer may be selected by performing an iterative function to reach predetermined thermomechanical properties, such as glass transition temperature ($T_g$) and rubbery modulus. Other thermomechanical properties to be considered in determining the weight percentages of the first and second monomer may include a desired predeformation temperature ($T_d$), storage temperature ($T_s$), recovery temperature ($T_r$), or deployment time. The selection of the weight percentages of the first and second monomers may optimize the post-implantation memory shape properties of the SMP sealant composition.

For example, changing the percentage weight of a crosslinker in a SMP formulation may change both a glass transition temperature ($T_g$) of the SMP and a rubbery modulus of the SMP. In some embodiments, changing the percentage weight of a crosslinker will affect the glass transition temperature and the rubbery modulus of an SMP. In other embodiments, changing the percentage weight of crosslinker will affect a recovery time characteristic of the SMP.

Some properties of a SMP may be interrelated such that controlling one property has a strong or determinative effect on another property, given certain assumed parameters. For example, the force exerted by a SMP against a constraint (e.g., an endotracheal lumen) after the SMP has been activated may be changed through control of the rubbery modulus of the SMP. Several factors, including a level of residual strain in the SMP enforced by the constraint will dictate the stress applied by the SMP, based on the modulus of the SMP. The stress applied by the SMP is related to the force exerted on the constraint by known relationships.

Examples of constituent parts of the SMP formulation include monomers, multi-functional monomers, cross-linkers, initiators (e.g., photo-initiators), and dissolving materials (e.g., drugs such as antimicrobial compositions, or salts). Two commonly included constituent parts are a linear chain and a crosslinker, each of which are common organic compounds such as monomers, multi-functional monomers, and polymers.

A crosslinker, as used herein, may mean any compound comprising two or more functional groups (e.g., acrylate, methacrylate), such as any poly-functional monomer. For example, a multi-functional monomer is a polyethylene glycol (PEG) molecule comprising at least two functional groups, such as di-methacrylate (DMA), or the combined molecule of PEGDMA. The percentage weight of crosslinker indicates the amount of the poly-functional monomers placed in the mixture prior to polymerization (e.g., as a function of weight), and not necessarily any direct physical indication of the as-polymerized "crosslink density."

A linear chain may be selected based on a requirement of a particular application because of the ranges of rubbery moduli and recovery forces achieved by various compositions. In some embodiments, a lower recovery force and rubbery modulus may be used for a sealant composition for sealing a trachea with an endotracheal tube comprising a SMP made from a formulation with tert-butyl acrylate (tBA) as the linear chain. In other embodiments, other linear chains may be selected based on desired properties such as recovery force and rubbery modulus. See e.g., U.S. Patent Application No. 2009/0248141 by Shandas et al. published on Oct. 1, 2009, which is incorporated herein by reference.

Foam Polymer as Sealant Composition.

In some embodiments, an endotracheal tube with a sealant composition that is a space-occupying material, e.g., foam sponge, is placed into the trachea of the subject to circumferentially surround one or more longitudinal portion of the endotracheal tube. The foam sponge sealant composition may be configured to reversibly form a seal in a trachea of a mammalian subject to prevent ventilator associated pneumonia. The sealant composition, e.g., foam sponge, circumferentially surrounding the endotracheal tube may contain foam sponge deflated by aspiration and then inflated when exposed to atmospheric pressure following placement into the trachea of the subject. In some embodiments, the endotracheal tube may contain foam sponge that is compressible by a wrap material surrounding the outside of the foam layer. The sealant composition including the foam sponge layer may be released by physical removal or chemical removal of the wrap material surrounding the foam sponge layer following placement into the trachea of the subject. See e.g., U.S. Patent Application No. 2006/0107962 by Ward et al. published on May 25, 2006, which is incorporated herein by reference.

Temperature Monitoring and Control.

The endotracheal tube may contain a temperature monitoring and control system to allow repeated cooling and heating of the sealant composition. The repeated cooling and heating of the sealant composition will permit the associated phase transitions from a flowable liquid to a gel and from a gel to a flowable liquid. A temperature sensor may be incorporated in the inflatable cuff or in or next to the sealant composition surrounding the endotracheal tube. A cooling element may be installed in the lumen of the inflatable cuff or in a lumen next to the sealant composition surrounding the endotracheal tube. For example, thermistors and thermoelectric cooling elements suitable for temperature control systems are accurate to ±0.5° C. See, e.g., Omega Engineering Inc., Stamford, Conn.

Accurate measurement, monitoring and control of sealant composition pressure against the trachea or cuff pressure against the trachea are important to prevent ventilator associated pneumonia and complications associated with endotracheal tubes. The inflation pressure of the cuff or the sealant composition pressure of the endotracheal tube is important to prevent leakage of microbes into the lungs. However, inflation of anchor cuffs or sealant composition pressure may cause complications such as reduced tracheal blood flow, inflammation, or damage to cilia. Endotracheal tube cuff pressure or sealant composition pressure is recommended to be in the range of 20-30 cm $H_2O$. Endotracheal tube cuff pressure or sealant composition pressure is recommended to be monitored with a manometer. See e.g., Sengupta et al., *BMC Anesthesiology* 4: 8, 2004, which is incorporated herein by reference.

PROPHETIC EXEMPLARY EMBODIMENTS

Example 1

Construction of an Endotracheal Tube with a Thermo-Responsive Sealant to Prevent Ventilator Associated Pneumonia An endotracheal tube (ET) is constructed with a cuff and a sealant which responds to changes in temperature. An ET is constructed from polyvinylchloride with an inflatable cuff at the distal end. For example, an ET is fabricated with an airway tube 7.5 mm inside diameter and a spherical inflatable cuff (see e.g., Specification sheet: Mallinckrodt™ Hi-Lo ET Tube available from Covidien Corp., Mansfield, Mass. which is incorporated herein by reference). The inflatable cuff is manufactured with a thermo-responsive sealant surrounding the cuff. The sealant is a thermally responsive polymer which transitions from a flowable phase to a solid phase at temperatures close to body temperature, approximately 37° C. For example, a polymer of N-isopropylacrylamide (NIPAAm) has a phase transition temperature of approximately 37° C. At temperatures below 37° C. NIPAAm polymer is flowable and after entering the body and heating to 37° C. the polymer transitions to a gel (see e.g., U.S. Pat. No. 7,985,601 issued to Healy et al. on Jul. 26, 2011 which is incorporated herein by reference). The inflatable cuff is encapsulated in NIPAAm polymer by coating the cuff at approximately 21° C. and raising the temperature to establish a gel attached to the cuff. Methods to encapsulate objects in thermo-responsive polymers are described (see e.g., U.S. Pat. No. 8,394,059 issued to Sahatjian et al. on Mar. 12, 2013 which is incorporated herein by reference). The sealant may also contain antibiotics which are released over time to kill or inhibit microorganisms present in pharyngeal secretions or esophageal aspirates. For example, antimicrobial drugs such as ciprofloxacin, beta lactams, tetracycline, gentamycin and streptomycin may be incorporated in the sealant. Methods to incorporate antimicrobial drugs in polymers are described (see e.g., U.S. Pat. No. 7,985,601, Ibid.).

The ET contains a temperature monitoring and control system to allow repeated cooling and heating of the sealant and the associated phase transitions from a flowable liquid to a gel. A temperature sensor is incorporated in the inflatable cuff and a cooling element is installed in the lumen of the inflatable cuff. For example thermistors suitable for temperature control systems which are accurate to ±0.5° C. and thermoelectric cooling elements are available from Omega Engineering Inc., Stamford, Conn. The ET contains a controller with microcircuitry to control the cooling element, receive temperature data and receive wireless signals from medical personnel. For example, wireless signals from a caregiver may initiate a cooling cycle to reduce the cuff and sealant to approximately 22° C. for approximately 2 minutes followed by return to body temperature, approximately 37° C. Repeated cooling cycles may be programmed to "reseal" the sealant according to a predetermined schedule.

Example 2

Long Term Intubation of a Patient in a Coma with an Endotracheal Tube Containing a Sealant and Cooling Elements An endotracheal tube (ET) with a thermo-responsive sealant is used to prevent ventilator associated pneumonia (VAP) in a patient intubated for a long period due to head trauma. The patient is intubated using a largynoscope and the correct placement of the ET and its inflatable anchor cuff is confirmed by chest X-ray. Prior to intubation the ET including the inflatable cuff may be warmed to 37° C. to transform the sealant to a gel phase prior to intubation. To insure a tight seal between the tracheal wall and the inflatable anchor cuff the cuff is encapsulated in a thermo-responsive polymer (i.e., sealant) which fills any gaps or creases which might allow subglottic secretions and microbes to pass through the trachea to the lungs. Leaks allowing microbes access to the lungs are a significant cause of VAP (see e.g., U.S. Patent Application No. 2006/0107962 by Ward et al. published on May 25, 2006 which is incorporated herein by reference). To seal the gaps and creases between the inflatable cuff and the tracheal inner wall the thermo-responsive polymer is cooled and then heated to body temperature. At approximately 21° C. the sealant is fluid and flows into gaps and creases. Then as it warms to 37° C. the sealant forms a gel which creates a seal between the cuff and the tracheal wall. See Example 1 above for thermal properties and phase transitions of the sealant.

It may be necessary to renew the seal between the ET cuff and the tracheal wall due to esophageal peristalsis, coughing or movement of the tracheal wall relative to the ET. A healthcare worker transmits a wireless signal to the controller (microcircuitry) on the ET which initiates a cooling cycle in the inflatable cuff. The thermoelectric cooling element lowers the temperature to approximately 21° C. based on feedback from the thermistor temperature sensor in the inflatable cuff. After approximately 5 minutes at 21° C. the sealant transitions to a fluid state and flows into any gaps or creases which may have formed between the inflatable cuff and the tracheal inner wall. Next the microcontroller turns off the cooling element and the sealant is allowed to return to body temperature and transitions to a gel. Alternatively the microcontroller may be programmed to initiate a cooling/heating cycle according to a regular schedule, for example, every 12 hours, 7 days a week to reseal the interface between the inflatable cuff and the trachea inner wall.

Example 3

Construction of an Endotracheal Tube System with Multiple Anchor Cuffs that are Actively Inflated at Varying Pressures by a Controller An endotracheal tube (ET) is constructed with multiple inflatable cuffs which are independently controlled at varying pressures to prevent ventilator associated pneumonia (VAP) and avoid complications. An ET is constructed from polyvinylchloride with toroidal (i.e., donut-shaped) inflatable cuffs at the distal end. For example, an ET is fabricated with an airway tube 7.5 mm inside diameter and 3 toroidal inflatable cuffs positioned on the exterior wall near the distal end of the ET. Endotracheal tubes with single or multiple inflatable cuffs have been described (see e.g., Specification sheet: Mallinckrodt™ Hi-Lo ET Tube available from Covidien Corp., Mansfield, Mass. and U.S. Pat. No. 4,091,816 issued to Elam on May 30, 1978 which are incorporated herein by reference). The inflatable cuffs are constructed of polyurethane with a thickness of 7 μm (see e.g., Lorente et al., *Am. J. Respir. Care Med.* 176: 1079-1083, 2007 which is incorporated herein by reference). The inflatable cuffs are connected to independent air pumps that are controlled by a central controller with microcircuitry that responds to preprogrammed schedules and/or signals from sensors placed in the airway.

Accurate measurement, monitoring and control of cuff pressure are important to prevent VAP and complications associated with ETs. The inflation pressure of cuffs is very important to prevent leakage of microbes into the lungs, but inflation of anchor cuffs may cause complications such as reduced tracheal blood flow, inflammation and damage to cilia (see e.g., Sengupta et al., *BMC Anesthesiology* 4: 8, 2004, which is incorporated herein by reference).

The pressure in the inflatable cuffs is controlled by a controller, air pumps and sensors which detect pressure in the cuffs, inflammation and peristalsis in the airway. Each inflatable cuff is connected by a separate supply line to provide air to the cuff. An external air pump capable of generating air pressures between 20 and 50 cm $H_2O$ is connected to each cuff supply line (e.g., micropump for air is available from KNF Neuberger, Inc., Trenton, N.J.). Each pump is independently controlled to actively vary the pressure of each cuff. Pressure sensors are incorporated into the supply line for each inflatable cuff to monitor cuff pressure and to signal cuff pressures to the controller. Ultra-low pressure sensors with a range of 2.5 cm $H_2O$ to 75 cm $H_2O$ are available from Honeywell Corp., Morristown, N.J. The controller may be programmed to limit the time and pressure of an individual cuff. For example, to prevent complications due to reduced blood flow in the trachea, the product of cuff pressure and time may be limited to a maximum of 25 cm $H_2O\times20$ hours, or 500 cm-hr. Cuff pressure may be reduced after reaching the maximum value and increased at a later time. Alternate cuffs may be inflated or deflated to retain a barrier to microbes and gases while avoiding complications arising from cuff pressure on the tracheal wall.

Example 4

An Endotracheal Tube Device with a Cuff Comprised of Memory Shape Polymer Surrounding the Endotracheal Tube to Prevent Leakage of Microbes and Fluids into the Lungs An ET is constructed with external cuffs comprised of shape memory polymers which are responsive to temperature and pressure. An ET is constructed from polyvinylchloride with azimuthally located cuffs at the distal end. For example, an ET is fabricated with an airway tube 7.5 mm inside diameter and 3 circular cuffs positioned azimuthally on the exterior wall near the distal end of the ET. The cuffs are fabricated from a shape memory polymer (SMP) which changes shape in response to temperature and stress. For example a biocompatible SMP with a glass transition temperature (Tg) slightly greater than body temperature (e.g., approximately 40° C.) is polymerized in a mold to create three cuffs encircling the airway tube of the ET. Methods and compositions to create a biocompatible SMP with a desired Tg and a suitable degree of flexibility and tensile strength are known (see e.g., U.S. Patent Application No. 2009/0248141 by Shandas et al. published on Oct. 1, 2009 and Lendlein et al., *Biomacromolecules* 10: 975-982, 2009 which are incorporated herein by reference). For example a SMP polymerized using 40 wt % polyethylene glycol dimethacrylate (PEGDMA) as crosslinker and methyl-methacrylate (MMA) as the linear chain yields a SMP with a Tg of approximately 40° C. Methods to adjust the rubbery modulus, shape recovery time, and Tg of SMPs are described (see e.g., U.S. Patent Application No. 2009/0248141 Ibid.). Alternatively, custom designed SMPs can be obtained from Cornerstone Research Group, Inc., Dayton, Ohio (see the information sheet: Veriflex® Shape Memory Polymer available from CRG, Inc., Dayton, Ohio which is included herein by reference). The diameter of the SMP cuffs (approximately 25 mm) is selected to contact the walls of the trachea when the ET is in place and the SMP has its original shape. To activate the SMP cuffs a resistive heating line is incorporated in the cuffs which allows heating of the cuffs to 40° C. or more in order to reach their glass transition temperature. Prior to insertion of the ET (i.e., intubation) the SMP cuffs are activated and compressed to facilitate intubation. For example a sterile sleeve or a wrap may be used to compress the cuffs and reduce their diameter while they are activated (e.g., at 40° C.). The sleeve is left in place and the cuffs are allowed to return to room temperature and they adopt a compressed conformation. The sterile sleeve is removed prior to intubation and the SMP cuffs remain compressed during the procedure. The resistive heating lines are activated by electric current from external power supplies which heats the SMP cuffs to 40° C. The cuffs regain their original shape (extended) with a diameter of approximately 25 mm and contact the wall of the trachea. After heating for approximately 5 minutes to allow maximum recovery of shape (approximately 99%) the SMP cuffs are allowed to cool to ambient temperature in the trachea, approximately 37° C. The extended conformation of the SMP cuffs is retained at 37° C. and they provide a barrier and seal to prevent subglottic fluids and microbes from passing into the bronchi and lungs. Reactivation of the SMP cuffs by heating to 40° C. using the resistive heating lines may be repeated to "reset" the cuffs contacts with the tracheal wall. Microcircuitry on the ET controls delivery of electrical current to the resistive heating lines and receives signals from temperature sensors in the SMP cuffs to regulate their temperature.

Each recited range includes all combinations and subcombinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will recognize that there are various vehicles by which processes and/or systems and/or other technologies disclosed herein can be effected (e.g., hardware, software, and/or firmware), and that the preferred vehicle will vary with the context in which the processes and/or systems and/or other technologies are deployed. For example, if a surgeon determines that speed and accuracy are paramount, the surgeon may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies disclosed herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those having ordinary skill in the art will recognize that optical aspects of implementations will typically employ optically-oriented hardware, software, and or firmware.

In a general sense the various aspects disclosed herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices disclosed herein, or a microdigital processing unit configured by a computer program which at least partially carries out processes and/or devices disclosed herein), electrical circuitry forming a memory device (e.g., forms of random access memory), and/or electrical circuitry forming a communications device (e.g., a modem, communications switch, or optical-electrical equipment). The subject matter disclosed herein may be implemented in an analog or digital fashion or some combination thereof.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device comprising:
   an endotracheal tube having an interior surface and an exterior surface;
   one or more closed cell layers in contact with the exterior surface and circumferentially surrounding one or more longitudinal portion of the endotracheal tube, wherein the one or more closed cell layers are flexibly shaped to reversibly form a seal in a trachea of a mammalian subject;
   a temperature sensor positioned to measure the temperature of one or more of the one or more closed cell layers and the endotracheal tube; and
   a controller configured to control a temperature control element in response to a temperature measurement from the temperature sensor.

2. The device of claim 1 comprising:
   two or more of the one or more closed cell layers circumferentially surrounding two or more immediately adjacent exterior longitudinal portions of the endotracheal tube.

3. The device of claim 1, wherein the one or more closed cell layers are reversibly compressible closed cell foam layers.

4. The device of claim 1, wherein the one or more closed cell layers include shape memory polymer or syntactic foam.

5. The device of claim 4, wherein the shape memory polymer has a glass transition temperature at or above 39° C. and at or below 40° C.

6. The device of claim 4, wherein the shape memory polymer has a glass transition temperature at or above 40° C. and at or below 41° C.

7. The device of claim 4, wherein the shape memory polymer has a glass transition temperature at or above 41° C. and at or below 42° C.

8. The device of claim 4, wherein the shape memory polymer has a glass transition temperature at or above 42° C. and at or below 44° C.

9. The device of claim 4, wherein the shape memory polymer has a glass transition temperature at or above 44° C. and at or below 50° C.

10. The device of claim 1, wherein the one or more closed cell layers is configured to seal the endotracheal tube in a trachea of a mammalian subject by contacting the exterior surface of the endotracheal tube and contacting a tracheal tissue of the subject.

11. The device of claim 1, comprising a cuff on the exterior surface of the endotracheal tube in contact with the one or more closed cell layers.

12. The device of claim 3, wherein the temperature control element comprises one or more of a heating element and a cooling element.

13. The device of claim 12, wherein the heating element is in thermal contact with the one or more closed cell foam layers.

14. The device of claim 12, wherein the cooling element is in contact with the one or more closed cell foam layers.

15. The device of claim 12, wherein the heating element is in thermal contact with the endotracheal tube.

16. The device of claim 12, wherein the cooling element is in thermal contact with the endotracheal tube.

17. The device of claim 1, comprising a bacteriostatic agent or a bacteriocidal agent in the one or more closed cell layers.

* * * * *